US006846482B2

(12) United States Patent
Liu et al.

(10) Patent No.: US 6,846,482 B2
(45) Date of Patent: Jan. 25, 2005

(54) INSECT CONTROL AGENT

(75) Inventors: Leo Liu, Weston, MA (US); Scott Chouinard, Medford, MA (US); James Velema, Somerville, MA (US)

(73) Assignee: Cambria Biosciences, Woburn, MA (US)

( * ) Notice: Subject to any disclaimer, the term of this patent is extended or adjusted under 35 U.S.C. 154(b) by 0 days.

(21) Appl. No.: 09/928,463

(22) Filed: Aug. 13, 2001

(65) Prior Publication Data

US 2002/0137710 A1 Sep. 26, 2002

Related U.S. Application Data

(63) Continuation of application No. 09/448,256, filed on Nov. 24, 1999, now Pat. No. 6,326,193.
(60) Provisional application No. 60/164,078, filed on Nov. 5, 1999.

(51) Int. Cl.[7] ...................... A61K 48/00; C12N 15/866; C07H 21/02; C07H 21/04
(52) U.S. Cl. ...................... 424/93.2; 424/93.1; 424/936; 514/2; 514/44; 435/235.1; 435/320.1; 435/69.1; 435/91.1; 435/455; 435/456; 435/325; 435/348
(58) Field of Search .................. 435/235.1, 320.1, 435/69.1, 91.1, 455, 456, 325, 398; 424/93.1, 93.2, 93.6; 514/2, 44

(56) References Cited

U.S. PATENT DOCUMENTS

| | | | |
|---|---|---|---|
| 5,077,214 A | | 12/1991 | Guarino et al. |
| 5,162,222 A | | 11/1992 | Guarino et al. |
| 5,169,784 A | | 12/1992 | Summers et al. |
| 5,298,612 A | * | 3/1994 | Jennings et al. ............ 536/23.2 |
| 5,674,485 A | | 10/1997 | Hammock et al. |
| 5,756,340 A | | 5/1998 | Hammock et al. |
| 5,759,809 A | | 6/1998 | Iatrou |
| 5,763,400 A | * | 6/1998 | Adams et al. ................ 514/12 |
| 5,770,192 A | | 6/1998 | Cayley et al. |
| 5,795,715 A | | 8/1998 | Livache et al. |
| 5,858,353 A | | 1/1999 | Miller et al. |
| 5,885,569 A | | 3/1999 | Windass |
| 5,925,346 A | | 7/1999 | Krause et al. |
| 5,959,182 A | | 9/1999 | Atkinson et al. |
| 5,985,269 A | | 11/1999 | Hammock et al. |
| 5,989,541 A | | 11/1999 | Iatrou |
| 6,087,165 A | | 7/2000 | Raina et al. |
| 6,096,304 A | | 8/2000 | McCutchen |
| 6,235,278 B1 | * | 5/2001 | Miller et al. ................ 424/93.2 |
| 6,326,193 B1 | * | 12/2001 | Liu et al. .................. 435/320.1 |

FOREIGN PATENT DOCUMENTS

WO       WO 99/32619       7/1999

OTHER PUBLICATIONS

Montgomery et al., "RNA as a Target of Double–Stranded RNA–Mediated Genetic Interference in Caenorhabditis Elegans" *Proceedings of the National Academy of Sciences of USA*, 95: 15502–15507, 1998.

Vermehren, et al., "Using RNA Interference to Study the Subunit Composition of Nicotinic Receptors in Manduca Sexta", Society for Neuroscience Abstracts, 26(1–2): 0190–5295, 2000.

Brown, et al., "Using RNAi to Investigate Orthologous Homeotic Gene Function During Development of Distantly Related Insects", *Evolution & Development*, 1(1): 11–15, 1999.

Chouinard, et al., "A Potassium Channel Subunit Related to the Aldo–Keto Reductase Superfamily is Encoded by the Drosophila Hyperkinetic Locus", *Proc. Natl. Acad. Sci. USA*, 92: 6763–67, 1995.

Davies, et al., "Analysis and Inactivation of vha55, The Gene Encoding the Vacuolar ATPase B–Subunit in Drosophila Melanogaster–Reveals a Larval Lethal Phenotype", *The Journal of Biological Chemistry*, 271(48): 30677–30684, 1996.

Dow, et al., "Molecular Genetic Analysis of V–ATPase Function in Drosophila Melanogaster", *The Journal of Experimiental Biology*, 200: 237–45, 1997.

Dow, et al., "The Multifunctional Drosophila Melanogaster—V–ATPase Is Encoded by a Multigene Family", *Journal of Bioenergetics and Biomembranes*, 31(1): 75–83, 1999.

Fire, et al., "Potent and Specific Genetic Interference by Double–Stranded RNA in Caenorhabditis Elegans", *Nature*, 391: 806–11, 1998.

Fire, et al., "Potent and Specific Genetic Interference by Double–Stranded RNA in Caenorhabditis Elegans", *Nature*, 391: 806–11, 1998.

Fire, "RNA–Triggered Gene Silencing", *TIG*, 15(9): 358–63, 1999.

Hajós, et al., "Dissecting Insect Development: Baculovirus–Mediated Gene Silencing in Insects", *Insect Molecular Biology*, 8(4): 539–44, 1999.

Hughes, et al., "RNAi Analysis of Deformed, Proboscipedia and Sex Combs Reduced in the Milkweed Bug Oncopeltus Fasciatus: Novel Roles for Hox Genes in the Hemipteran Head", *Development*, 127: , 3683–94, 2000.

(List continued on next page.)

*Primary Examiner*—David Guzo
(74) *Attorney, Agent, or Firm*—Choate, Hall & Stewart; Monica R. Gerber; Brenda H. Jarrell

(57) ABSTRACT

The invention includes an expression vector engineered to produce double-stranded RNA (dsRNA) within a pest to be controlled. The dsRNA inhibits expression of at least one gene within the pest, wherein inhibition of the gene exerts a deleterious effect upon the pest. For example, inhibition of the gene can lead to cessation of feeding, growth, or development and can cause death of the pest. In a preferred embodiment of the invention the expression vector is a recombinant baculovirus that transcribes sense and antisense RNA under the control of the baculovirus IE-1 promoter and hr5 enhancer. Preferred genes to be inhibited include essential genes, genes involved in neurotransmission, and genes that are targets for conventional pesticides. The invention discloses baculovirus transfer plasmids useful for producing the recombinant baculovirus. The invention further discloses methods and formulations involving the expression vector.

32 Claims, 9 Drawing Sheets

OTHER PUBLICATIONS

Johnson, et al., "Inhibition of Luciferase Expression in Transgenic Acedes Aegypti Mosquitoes by Sindbis Virus Expression of Antisense Luciferase RNA", *PNAS*, 96(23): 13399–13403, 1999.

Kennerdell, et al., "Heritable Gene Silencing in Drosophila Using Double–Stranded RNA", *Nature Biotechnology*, 18: 896–98, 2000.

Kennerdell, et al., "Use of dsRNA–Mediated Genetic Interference to Demonstrate that Frizzled and Frizzled 2 Act in the Wingless Pathway", *Cell*, 95: 1017–26, 1998.

Lewis, et al., "Distinct Roles of the Homeotic Genes Ubx and abd–A in Beetle Embryonic Abdominal Appendage Development", *PNAS*, 97(9): 4504–09.

Marie, et al., "Double–Stranded RNA Interference Shows that Engrailed Controls the Synaptic Specificity of Indentified Sensory Neurons", *Current Biology*, 10: 289–92: 2000.

Misquitta, et al., "Targeted Disruption of Gene Function in Drosophila byRNA Interference (RNA–1): A Role for Nautilus in Embryonic Somatic Muscle Formation", *Proc. Natl. Acad. Sci.* 96: 1451–56, 1999.

Montgomery, et al., "Double–Stranded RNA as a Mediator in Sequence–Specific Genetic Silencing and Co–Suppression", *TIG*, 14(7): 255–58, 1998.

Oppenheimer, et al., "Functional Conservation of the Wingless–Engrailed Interactions as Shown by a Widely Applicable Baculovirus Misexpression System", *Current Biology*, 9: 1288–96, 1999.

Roelvink, et al., "Dissimilar Expression of Autographa California Multiple Nucleocapsid Nuclear Polyhedrosis Virus Polyhedrin and p10 Genes", *Journal of General Virology*, 73: 1481–89, 1992.

Ruiz, et al., "Initiation and Maintenance of Virus–Induced Gene Silencing", *The Plant Cell*, 10: 937–46, 1998.

Timmons, et al., "Specific Interference by Ingested dsRNA", *Nature*, 395: 854, 1998.

Wieczorek, et al., "The Plasma Membrane $H^+$–V–ATPase from Tobacco Hornworm Midgut", *Journal of Bioenergetics and Biomembranes*, 31(1): 67–74, 1999.

Wood, et al., "Genetically Engineered Baculoviruses as Agents for Pest Control", *Annu. Rev. Microbiol.* 45: 69–87, 1999.

\* cited by examiner

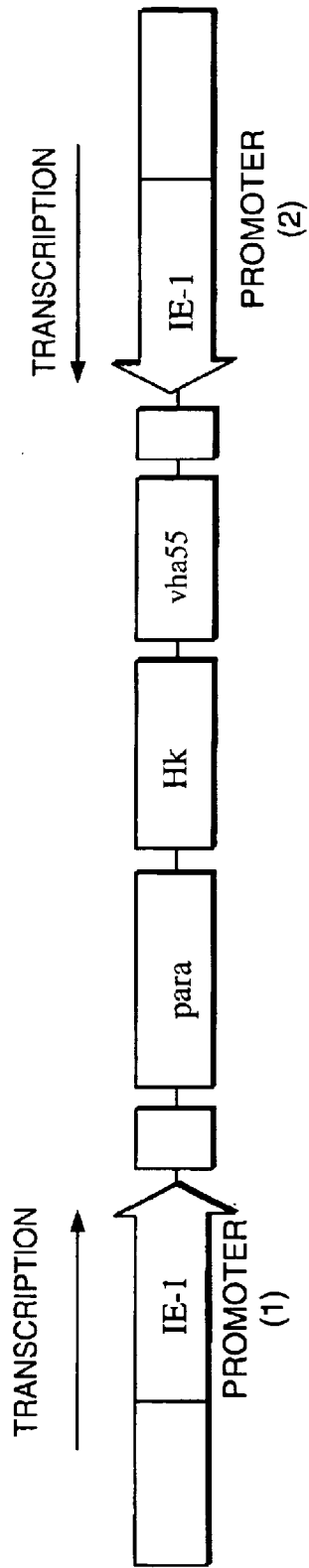
FIG. 5A
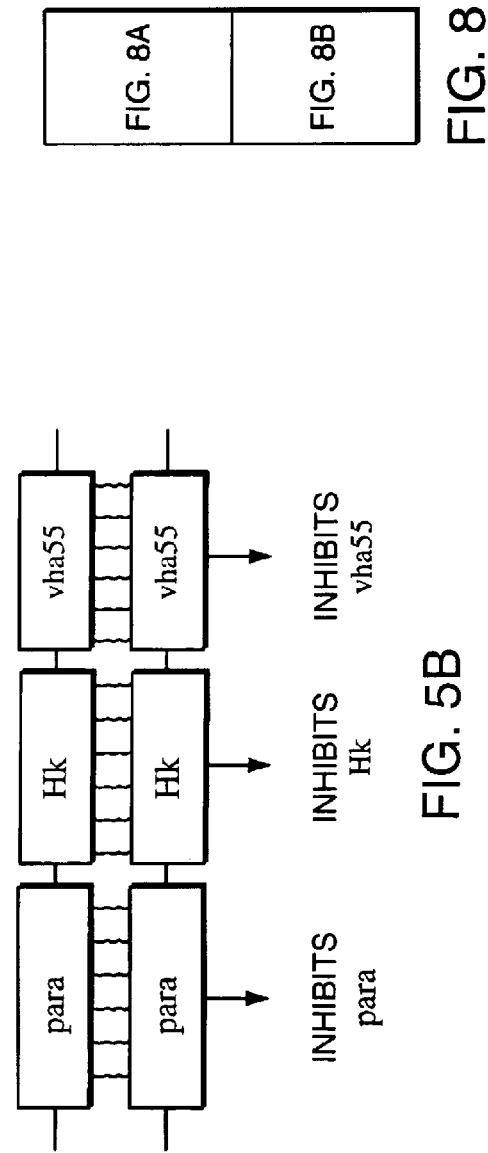
FIG. 5B
FIG. 8

SV40 Transcriptional Terminator Sequence

SEQ ID NO:1

TGATCATAATCAGCCATACCACATTTGTAGAGGTTTTACTTGCTTTAAAAAAC
CTCCCACACCTCCCCCTGAACCTGAAACATAAAATGAATGCAATTGTTGTTGT
TAACTTGTTTATTGCAGCTTATAATGGTTACAAATAAAGCAATAGCATCACAA
ATTTCACAAATAAAGCATTTTTTTCACTGCATTCTAGTTGTGGTTTGTCCAAAC
TCATCAATGTATCTTAA

FIG. 8A

Primers Used in Construction of Modified Baculovirus Transfer Vectors

SEQ ID NO:2  SV40Xba#2  AAAATCTAGATCATAATCAGCCATACC

SEQ ID NO:3  SV40SacII  CCGCGGTTAAGATACATTGATGAGTTTGG

SEQ ID NO:4  SV40Bam#2  AAAAGGATCCATTGATGAGTTTGGACAAACC

SEQ ID NO:5  IE1-3.5'  ACTAGTTATCTCCATGATGGGCGCG

SEQ ID NO:6  IE1-6.5'  AGATCTATATAGTTGCTGATGGGCGCG

Primers Used to Amplify Portions of Target Genes from Drosophila melanogaster

Dm.para primers

SEQ ID NO:8  Dm.para5'  5'- TGAGGAAGAACGCAGTTTGTTCC -3'

SEQ ID NO:9  Dm.para3'  5'- CGGGCATAAAATGAAACCTCG -3'

Dm.white primers

SEQ ID NO:10  White5'  5'- CGCTGTGACACATACTTTCTG -3'

SEQ ID NO:11  White3'  5'- GTCTTAGAGCCAGATATGCG -3'

Dm.vha55 (subunit B) primers for 3'UTR

SEQ ID NO:12  DmvB5'  5'- TCTCCACCTCCTGCAATATCCG -3'

SEQ ID NO:13  DmvB3'  5'- CCCATTCACTCTTGTGACCAGAG -3'

Dm.vha26 (subunit E) primers for 3'UTR

SEQ ID NO:14  DmvE5'  5'- ACCAGAAAGAGAACCAGCATCAAC -3'

SEQ ID NO:15  DmvE3'  5'- ACCTGCCAGCGGTCTGTAAAAG -3'

FIG. 8B

**Primers Used to Amplify Portions of Target Genes from *Manduca sexta***

Manduca para primers
SEQ ID NO:16    para5'    5'- TGCATGGAATTGGCTTGACTTC -3'

SEQ ID NO:17    para3'    5'- AGCACCAGTTGATAGAGATTCTCCC -3'

Manduca hb PCR Primers
SEQ ID NO:18    Ms.hb.5'    5'- CTCGTTCTTATTCCCTCCTAAC -3'

SEQ ID NO:19    Ms.hb.3'    5'- ATGAACGGGTCGTTGTACC -3'

Manduca fasciclinII primers
SEQ ID NO:20    fas5'    5'- TACTGCACCAGAAATGGAAGAGC -3'

SEQ ID NO:21    fas3'    5'- ACGGGTTGGTTGTTCATAGCC -3'

Manduca EcR primers
SEQ ID NO:22    Ms.EcR.5'    5'- CGTGCAACGTGCTCGTTTTTAC -3'

SEQ ID NO:23    Ms.EcR3'    5'- TTAGGAGTTGTAGGAGGCATCGG -3'

Manduca vha55 (subunit B) primers for 3'UTR
SEQ ID NO:24    MsvB5'    5'- GATCTGGTTTCGATTGTTTCCG -3'

SEQ ID NO:25    MsvB3'    5'- CGAGGACCAACTCAATTTGGAATG -3'

Manduca vha26 (subunit E) primers for 3'UTR
SEQ ID NO:26    MsvE5'    5'- GGTGACCCACATTCACTCGTTATAC -3'

SEQ ID NO:27    MsvE3'    5'- AACCTACAGACCTCAATGCCTCC -3'

FIG. 9

Portion of Multiple Cloning Site from Plasmid PCR2.1 Incorporated into Modified Baculovirus Transfer Plasmids

SEQ ID NO:7

AGCCGAATTCTGCAGATATCCATCACACTGGCGGCCGCTCGAGCATGCATCTAGA

INSECT CONTROL AGENT

This application is a continuation of U.S. patent application Ser. No. 09/448,256, filed Nov. 24, 1999, now U.S. Pat. No. 6,326,193, which is incorporated by reference herein. This application claims the benefit of priority to U.S. Provisional Patent Application 60/164,078, filed Nov. 5, 1999, which is also incorporated by reference herein.

BACKGROUND OF THE INVENTION

Modern agricultural practice relies heavily on the use of insecticides and nematicides to improve crop yields. The vast majority of pesticides are chemical agents. As has been widely recognized, the use of chemical pesticides has a number of disadvantages. Conventional chemical insecticides frequently act nonspecifically, killing beneficial insect species in addition to the intended target. Chemicals may persist in the environment and present a danger to organisms higher up in the food chain than the insect pest. Exposure to chemical pesticides is hazardous and poses a threat to the health of agricultural workers and others. In addition, with repeated applications of pesticides resistant pest populations frequently emerge.

Biological pest control agents provide an attractive alternative to the use of chemicals. The term "biological pest control agent" refers to a naturally occurring agent that, when contacted with a pest, is able to infect the pest and interfere with its normal functioning so as to bring about the incapacitation or death of the pest. As used herein, "biological pest control agents" include naturally occurring agents that have been modified in certain ways. In the context of insect control, such agents comprise primarily viruses and bacteria. Insect control strategies utilizing biological control agents take advantage of the naturally occurring interactions between the agent and its insect hosts. The use of viruses and bacteria as pest control agents capitalizes on features such as the ability to enter target cells and exert pathogenic effects.

Biological pest control agents have the potential to be much more specific in terms of their targets than chemical pesticides affecting only insects within the host range of the virus or bacterium. Specificity, while desirable from the standpoint of maximizing safety and minimizing environmental impact, is also a potential disadvantage. In most settings multiple pest species are present, and it is not cost effective to deliver multiple different insecticides rather than a single agent with a broad spectrum of activity. The present invention addresses this and other limitations of prior art biological pest control agents.

A wide variety of viruses selectively infect insects, and the use of many of these as potential insect control agents has been explored (discussed in Miller, L. and Ball, L. A., eds., *The Insect Viruses*, New York, 1998). In particular, use of baculoviruses as biological insect control agents has been the subject of much research over the past three decades. Baculoviruses are double-stranded DNA viruses that specifically infect arthropods. Most baculoviruses under consideration as biological insect control agents have host ranges limited to the order Lepidoptera. In a typical baculovirus infection, larvae feeding on a plant contaminated with virus ingest the virus. If a susceptible insect ingests sufficient quantity of virus, a productive systemic infection ensues. Infection is most severe if established during an early larval stage. Depending on the stage of infection and other variables such as dose, temperature, and nutrition, death usually occurs within one to ten days, most commonly between four and seven days.

The baculovirus replication cycle has been extensively studied (reviewed in Miller, L. ed., *The Baculoviruses*, New York, 1997, the contents of which are incorporated herein by reference). The first step is adsorption of the virus to the surface of a host cell. A specific molecular target on the cell surface has not been identified. After ingestion by an insect, entry through the midgut is believed to occur by direct fusion of the viral envelope with the cell membrane. Uncoating of the viral DNA occurs following viral entry. In host cells able to support a productive infection, the viral DNA enters the cell nucleus, where gene expression takes place.

Baculovirus genes are expressed sequentially, in a temporally regulated manner. Baculovirus genes are divided into immediate-early, delayed early, late, and very late genes based upon the phase of the viral replicative cycle in which they are expressed. Temporal control is likely achieved by a cascade of transcriptional regulation in which the transcription of later genes depends upon the presence of gene products produced earlier. Transcription of immediate-early genes begins soon after viral entry into the nucleus and does not require viral gene products, relying instead on host transcriptional machinery. Temporal control of transcription is a characteristic of many viruses.

One well-characterized baculovirus immediate-early gene is known as IE1. Other immediate early gene promoters include IEN and IE0. Examples of very late genes include the polyhedrin and P10 genes. Expression from the polyhedrin and P10 promoters requires the activity of viral gene products produced at earlier stages of the replicative cycle. Thus genes under the control of the polyhedrin or P10 promoters can occur only in baculovirus-infected cells during the very late phase of the infection (Guarino et al., U.S. Pat. Nos. 5,077,214 and 5,162,222 and references therein).

In addition to promoter elements the baculovirus genome contains enhancer elements that enhance transcription from promoters to which they are linked. In particular, the enhancer elements hr1, hr2, hr3, hr4, and hr5 enhance expression from immediate early gene promoters (Guarino et al., U.S. Pat. Nos. 5,077,214 and 5,162,222 and references therein).

Baculoviruses occur in two forms. Mature viral particles (nucleocapsids) can be packaged in occlusion bodies within the nucleus of infected cells. Occlusion bodies consist primarily of polyhedrin, a viral protein expressed very late in the replicative cycle, and nucleocapsids. Occlusion bodies, typically containing large numbers of viral particles are released into the environment upon death of the host cell or insect and are able to withstand environmental stresses for long periods of time. The occlusion body structure thus protects the virus until ingestion by a susceptible host and mediates transmission from one organism to another. Baculoviruses can also bud from the membrane of the host cell, acquiring a membranous envelope as they do so. This so-called nonoccluded form is the means by which the virus spreads from cell to cell within the host. Nonoccluded viral particles are rapidly degraded upon exposure to the environment. In the absence of polyhedrin, e.g., in the case of infection by baculoviruses lacking the polyhedrin gene, only nonoccluded viral particles are produced.

Recombinant baculoviruses are widely used for the production of foreign proteins in insect cell lines. Rather than modifying the viral genome directly, creation of recombinant baculoviruses utilizes transfer plasmids. These plasmids generally contain sequences that permit them to replicate in bacteria, allowing convenient manipulation. In addition, they contain a baculovirus promoter capable of driving expression of a foreign gene operably linked to the promoter and a multiple cloning site into which such a foreign gene can be inserted. Some transfer plasmids incorporate additional genetic control elements such as enhancers and transcriptional terminators. Selectable markers such as drug resistance genes and markers whose presence can be readily detected, e.g., the beta-galactosidase gene, may be included to facilitate molecular biological manipulations and selection of recombinant baculoviruses. The multiple cloning site and genetic control elements are flanked by sequences homologous to a portion of the baculovirus genome, thus targeting the plasmid for insertion into baculovirus DNA. Transfer plasmid can be used to produce either occlusion-positive or occlusion-negative baculovirus recombinants depending upon whether a functional polyhedrin gene is present in the recombinant.

There is evidence that baculovirus diseases occur in at least 500 different insect species including many of the most significant pests of agricultural and forestry crops. However, individual baculovirus strains are usually restricted in their replication to one or a few insect species. Thus pathogenic effects that require viral replication can be targeted to the species for which control is sought. Some baculoviruses, e.g., members of the *Autographa californica* nuclear polyhedrosis virus (AcNPV) family, can replicate at some level in a wide variety of Lepidopteran hosts.

Although highly attractive from the standpoint of environmental safety, development of baculoviruses as biological insect control agents has proven problematic. The generally prolonged time from viral exposure to death, during which larvae continue to damage the plant, has meant that in most cases unmodified baculoviruses are not viable alternatives to chemicals, which halt larval crop damage almost immediately upon contact.

Three general approaches have been employed in attempts to improve the efficacy of baculoviruses as pest control agents by genetically modifying the virus. One approach has been to utilize viruses in which certain baculovirus genes that may prolong the life of the host have been inactivated or deleted from the viral genome (e.g., U.S. Pat. No. 5,858,353). A second approach has been to use the virus to direct inappropriate expression of insect genes that normally regulate important aspects of insect physiology or development, with the goal of interfering with key physiological or developmental processes such as fluid balance or molting. Among the genes that have been utilized are those encoding diuretic hormone, juvenile hormone esterase, and prothoracicotropic hormone (reviewed in Black et al., "Commercialization of Baculoviral Insecticides" in Miller, L. (ed.), *The Baculoviruses*, 1997). A third approach has been to engineer baculoviruses to express insecticidal toxins, primarily insect-specific toxins that are found in the venom of organisms that prey on insects (Maeda, S., et al., 1991, Stewart, L., et al., 1991, Windass, J., U.S. Pat. No. 5,885,569). Most of these toxins target the insect nervous system, which is also the site of activity of commercial chemical insecticides.

Although these three types of modifications have resulted in some enhancement of the speed of activity of baculovirus insecticides, chemical insecticides still act significantly faster. One limitation of all three approaches is that, just as with unmodified baculovirus insecticides, they are likely to require the establishment of a productive infection involving viral replication in order to be effective.

SUMMARY OF THE INVENTION

The present invention provides a biological pest control agent that causes production of a double-stranded RNA (dsRNA) within an organism. The invention encompasses the finding that dsRNA corresponding to a portion of a target gene inhibits expression of the target gene. It is well known that many genes play important or even essential roles in feeding, development, and survival in particular organisms. Inhibiting these genes can cause effects ranging from cessation of feeding to death, thus providing an effective means of controlling pest damage to plants.

A pest control agent of the present invention includes an expression vector that directs the synthesis of dsRNA corresponding to a particular gene or genes. In a preferred embodiment the expression vector comprises a recombinant virus containing genetic control elements operably linked to a DNA segment that includes at least a portion of an insect gene, wherein the genetic control elements direct expression of dsRNA corresponding to the insect gene portion, so that expression of the insect gene is inhibited when the insect is contacted with the virus. In a particularly preferred embodiment of the invention the recombinant virus is a baculovirus. Thus the invention provides a recombinant baculovirus that directs expression of a dsRNA corresponding to at least a portion of an insect gene when the virus is present in an insect cell. In certain embodiments of the invention the dsRNA is transcribed by the host transcriptional machinery. In certain preferred embodiments of the invention production of dsRNA does not require significant viral replication.

In another aspect, the invention provides plasmids containing genetic control elements and a site for insertion of a DNA segment, so that the genetic control elements direct transcription of dsRNA corresponding to an inserted DNA segment.

The invention further provides baculovirus transfer plasmids containing genetic control elements operably linked to at least a portion of an insect gene, so that the genetic control elements direct transcription of dsRNA corresponding to the gene portion. Transfer plasmids of the present invention are useful in the creation of the inventive recombinant viruses described herein.

An insect gene suitable for use in the present invention is one whose protein product is required for the insect to maintain its normal physiological and biochemical functions. Stated another way, lack of the protein significantly impairs growth or survival of the insect. In accordance with results described below, the dsRNA inhibits expression of the gene to which it corresponds, i.e., the target gene. Inhibition of the target gene limits the insect's ability to feed, grow, or survive. Examples of insect genes that may be employed in the practice of the invention include essential genes, genes involved in processes such as development, metabolism, or neurotransmission, and genes whose products are targets of existing insecticides.

A recombinant virus of the present invention comprises at least a portion of a target gene, operably linked to the genetic control elements necessary for synthesis of sense and anti-sense RNA. In some embodiments of the invention the gene, or portion thereof, and necessary genetic control elements may be inserted directly into the viral genome. In certain preferred embodiments the gene, or portion thereof, and necessary genetic control elements are first inserted into a plasmid that is ultimately used to produce a recombinant virus as described below.

The invention additionally provides methods of inhibiting expression of a target gene by contacting a pest with a recombinant virus engineered to produce dsRNA. The invention further provides compositions and methods for controlling pests by contacting the pests with a recombinant virus engineered to produce dsRNA.

DEFINITIONS

Antisense—As used herein refers to a single-stranded nucleic acid, typically RNA, having a complementary base sequence to the base sequence of a messenger RNA (mRNA).

Complementary—As used herein refers to a nucleotide sequence that is related to another nucleotide sequence by the Watson-Crick base-pairing rules, i.e., the sequence A-T-G-C in a DNA strand is complementary to the sequence T-A-C-G in a second DNA strand and to the sequence U-A-C-G in an RNA strand.

Double-stranded RNA (dsRNA)—As used herein refers to a polyribonucleotide structure formed by either a single self-complementary RNA strand or by at least two complementary RNA strands. The degree of complementary need not necessarily be 100 percent. Rather, it must be sufficient to allow the formation of a double-stranded structure under the conditions employed.

Early gene—A viral gene that is transcribed prior to the onset of viral DNA replication, i.e., early during infection. In the case of baculovirus, early gene promoters are thought to be responsive to host cell RNA polymerase II and host transcription factors.

Essential gene—Considered in reference to a single cell, an essential gene is one required for the cell to survive. Considered in reference to an organism, an essential gene is one that is required in at least some cells of the organism, in order for the organism to grow or survive.

Gene expression or expression—As used herein refers to the presence of an RNA transcribed from a gene or a protein translated from an RNA transcribed from the gene within a cell, tissue, or organism. More specifically, gene expression can be evaluated with respect to RNA expression or protein expression. The term "gene expression" is also used to refer to the process by which RNA is transcribed from a gene or by which RNA transcribed from a gene is translated.

Immediate early gene—A viral gene that is transcribed very shortly after infection, i.e., within less than 60 minutes after entry of virus into a cell.

Null phenotype—The phenotype that results when a gene is deleted or modified in such a way that no functional protein product is produced.

Nonproductive viral infection—As used herein refers to a process in which a virus enters host cells but where such entry does not ultimately result in production of new, fully formed viruses. The virus may undergo some, but not all, of the steps required to form new virus.

Productive viral infection—As used herein refers to a process in which a virus enters a host and replicates within the host, so that new, fully formed viruses are produced.

Recombinant virus—As used herein refers to a virus whose genome contains at least one DNA segment not naturally found in the genome of the virus.

Replicate—As used herein refers to the process by which a virus produces, or directs the production of, functional copies of itself. Viral replication necessarily includes replication of viral DNA.

Sense—As used herein, refers to a base sequence as present in a messenger RNA (mRNA).

Vector—As used herein, refers to a nucleic acid molecule capable of mediating introduction of another nucleic acid to which it has been linked into a cell. One type of preferred vector is an episome, i.e., a nucleic acid capable of extrachromosomal replication. Preferred vectors are those capable of extra-chromosomal replication and/or expression of nucleic acids to which they are linked in a host cell. Vectors capable of directing the expression of inserted DNA sequences are referred to herein as "expression vectors" and may include plasmids or viruses, in particular baculoviruses. However, the invention is intended to include such other forms of expression vector which serve equivalent functions and which become known in the art subsequently hereto.

ABBREVIATIONS

As used herein *Drosophila* refers to the fruit fly *Drosophila melanogaster* (abbreviated Dm), and *Manduca* refers to the tobacco hornworm *Manduca sexta* (abbreviated Ms).

BRIEF DESCRIPTION OF THE DRAWING

FIG. 5A is a diagram of a composite DNA segment for insertion into a transfer plasmid.

FIG. 5B is a diagram of the dsRNA molecule produced by hybridization of RNA corresponding to each DNA subsegment of FIG. 5A with its complementary RNA.

FIG. 8 (Parts A–B) presents sequences incorporated into modified baculovirus transfer plasmids and sequences of primers used to amplify portions of target genes.

FIG. 9 is the sequence of 55 nucleotides of the multiple cloning site from plasmid PCR2.1 that were incorporated into the modified baculovirus transfer plasmids.

DETAILED DESCRIPTION OF CERTAIN EMBODIMENTS

Figure 1:
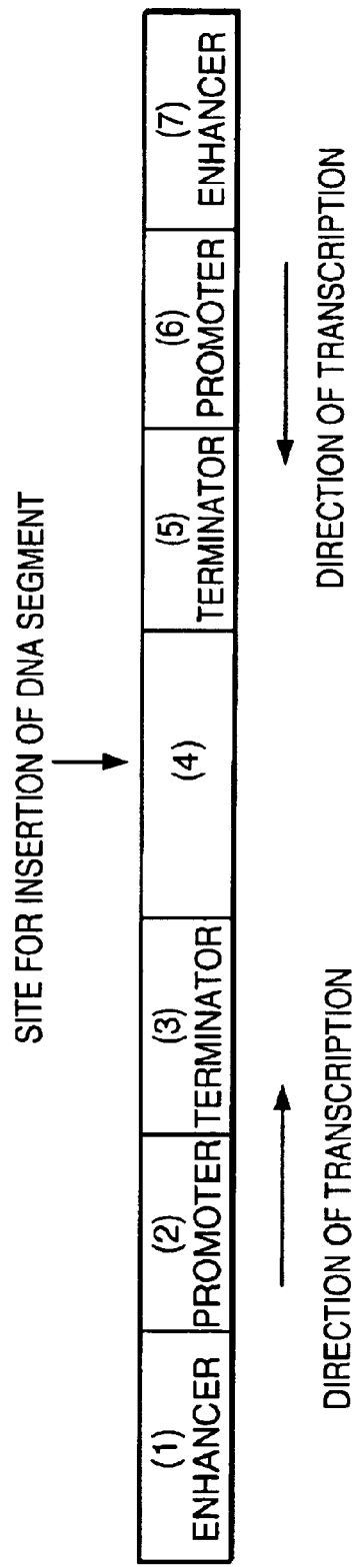
FIG. 1 is a diagram of the genetic elements capable of directing transcription of dsRNA from a DNA segment.

The present invention provides recombinant viruses for use as biological insect control agents. The viruses contain a portion of a selected insect gene and genetic elements operably linked to the portion of the gene so as to direct synthesis of dsRNA corresponding to the selected gene portion. Expression of the gene within the insect is inhibited when the insect is contacted with the virus. An insect control virus of the present invention interferes with expression of a gene that is essential for normal physiological or biochemical functioning of the insect. The effect of such inhibition on the insect ranges from cessation of feeding, growth, or normal development to death of the insect. Preferably the effect is observed within 24 hours after the insect comes into contact with the virus. Yet more preferably the effect is observed within 12 hours after the insect comes into contact with the virus. Yet more preferably the effect (e.g., cessation of feeding, growth, or normal development)

is observed with 4 to 8 or even fewer hours after the insect comes into contact with the virus.

The invention additionally provides methods of inhibiting expression of a target gene by contacting an insect with a recombinant virus engineered to produce dsRNA and further provides methods of controlling insect pests by contacting the insect pests with a recombinant baculovirus engineered to produce dsRNA.

The invention further provides plasmids that may be employed in the construction of a virus for control of insect pests. The plasmids contain genetic control elements and a site for insertion of a DNA segment. The plasmids also contain sequences that facilitate incorporation of certain portions of the plasmid, including the genetic control elements and inserted DNA segment, into a virus. The genetic control elements are arranged so that dsRNA corresponding to an inserted DNA segment is generated when the recombinant virus is introduced into an appropriate cell.

One way to interfere with gene function is to introduce antisense nucleic acids (RNA, DNA, or modified DNA) into cells. The sequence of the antisense molecule is complementary to that of an RNA molecule normally transcribed by the cell. Binding of the antisense molecule to the endogenous target RNA can inhibit expression of the target in any of several ways, e.g., by preventing ribosome binding and thus interfering with translation. One major limitation of the antisense strategy is that it requires the presence of antisense molecules at concentrations at least as high as the concentration of endogenous mRNA.

Antisense molecules can be delivered exogenously or by introducing into the cell a vector capable of directing transcription of an antisense RNA molecule. Baculovirus vectors have been employed for the production of antisense RNA in insects (e.g., Vlak and Chejanovsky, The XIVth International Plant Protection Congress Meeting Report, page 15, 1999). However, the magnitude of the observed effects suggested that antisense strategies are unlikely to produce sufficiently rapid effects on larval feeding and growth. In addition, to achieve sufficient synthesis of antisense molecules will probably require that the insect ingest large amounts of virus or that the virus replicate extensively within the host.

The present invention encompasses the finding that double-stranded RNA (dsRNA) can exert much more potent inhibitory effects on gene expression than antisense RNA. This phenomenon, known as double-stranded RNA interference (dsRNAi), has been extensively documented in the nematode *C. elegans* (Fire, A., et al, *Nature*, 391, 806–811, 1998). There is also evidence for the existence of a similar or identical phenomenon in plants, in which it is usually referred to as post-transcriptional gene silencing (PTGS) (Van Blokland, R., et al., *Plant J.*, 6: 861–877, 1994; deCarvalho-Niebel, F., et al., *Plant Cell*, 7: 347–358, 1995; Jacobs, J. J. M. R. et al., *Plant J.*, 12: 885–893, 1997; reviewed in Vaucheret, H., et al., *Plant J.*, 16: 651–659, 1998). The phenomenon also occurs in fungi (Romano, N. and Masino, G., *Mol. Microbiol.*, 6: 3343–3353, 1992, Cogoni, C., et al., *EMBO J.*, 15: 3153–3163; Cogoni, C. and Masino, G., *Nature*, 399: 166–169; 1999), in which it is often referred to as "quelling". The terms dsRNAi, PTGS, and quelling will be used interchangeably herein.

Although recognized in other organisms, much recent work has focused on the utilization of dsRNAi as a tool for studying gene function in *C. elegans*. It has been demonstrated that injection of dsRNA corresponding to a particular gene into the gonad or body cavity (intestine) of adult worms results in progeny with a phenotype similar or identical to that of a null mutant. Injection of dsRNA into young worms similarly inhibits expression of the target gene in the injected worm. Results of this kind have been obtained with a wide variety of genes, and it appears that virtually every gene can be inhibited using dsRNAi. Most commonly, annealing of the sense and antisense RNA strands is performed in vitro before delivery of the RNA to the organism. Experiments in which purified sense and antisense RNAs are injected sequentially demonstrate that dsRNAi also takes place when annealing occurs in vivo. dsRNAi also operates in the fruit fly *Drosophila melanogaster* and in other insects (Misquitta, L. and Paterson, B., *Proc. Natl. Acad. Sci., USA*, 96: 1451–1456, 1999; Kennerdell, J. and Carthew, R., *Cell*, 95: 1017–1026, 1998). However, it appears extremely unlikely that the dsRNA inhibition mechanism functions in mammalian cells (Fire, A., RNA-triggered gene silencing, *Trends in Genetics*, 15: 358–363, 1999).

Levels of dsRNA far below those of the endogenous transcript are sufficient to cause inhibition. Doses of dsRNA as low as one or several molecules per cell are effective. In addition, the inhibitory effect of dsRNA is able to cross cellular boundaries. Injection of dsRNA into the *C. elegans* body cavity or into one end of the gonad (a structure that extends through much of the length of the animal) resulted in inhibition in progeny derived from either end of the gonad and in somatic tissues throughout the injected worm. Inhibition can occur in up to 99% of cells in the organism.

The mechanism by which dsRNA inhibits gene expression is unclear. Introduction of dsRNA into a cell results in disappearance of the endogenous transcript. Transcription of the target locus appears to be unaffected, but there is a dramatic decrease in the half-life of the target RNA. The effect seems to be catalytic in that the amount of dsRNA required to cause disappearance of the endogenous transcript is as low as one to several molecules. A variety of mechanisms by which dsRNA may inhibit gene expression have been proposed, but evidence in support of any specific mechanism is lacking (Fire, A., 1999).

To provide effective inhibition, the dsRNA should meet several requirements, e.g., in terms of length and sequence identity to the gene to be inhibited. These requirements will be discussed in more detail below since they govern certain aspects of the preferred embodiments of the invention.

Synthesis of sense and antisense RNA can either be driven from separate promoters, or a single RNA molecule comprising sense and antisense sequences can be transcribed under the direction of a single promoter. In a preferred embodiment of the invention, a unit containing appropriate genetic elements and a site for insertion of a DNA segment is created. The unit contains two promoters in opposite orientation, so that both strands of a DNA segment inserted between the two promoters are transcribed. A preferred embodiment of the invention further includes an enhancer positioned on the opposite side of each promoter relative to the DNA segment insertion site, in an appropriate directional orientation to enhance transcription from the promoter. In other words the promoter is positioned between the enhancer and the DNA segment insertion site. In preferred embodiments a genetic element capable of directing termination of transcription is positioned downstream of each promoter/enhancer element so that transcripts driven from this promoter are terminated shortly after the end of the DNA segment being transcribed is reached.

Thus in a preferred embodiment, the unit into which the DNA segment is to be inserted contains the following elements, positioned from left to right (see FIG. 1):

(1) A DNA region including an enhancer.
(2) A DNA region including a promoter oriented in a 5' to 3' direction so that a DNA segment inserted into DNA region (4) is transcribed.
(3) A DNA region including a transcriptional terminator arranged in a 3' to 5' orientation so that a transcript synthesized in a right to left direction from the promoter of part (5) is terminated.
(4) A DNA region into which a DNA segment can be inserted. Preferably this region contains at least one restriction enzyme site.
(5) A DNA region including a transcriptional terminator arranged in a 5' to 3' orientation so that a transcript synthesized in a left to right direction from the promoter of part (3) is terminated.
(6) A DNA region including a promoter oriented in a 3' to 5' direction, i.e. in reverse orientation, so that a DNA segment inserted into DNA region (4) is transcribed.
(7) A DNA region including an enhancer.

The unit can be constructed in a plasmid or by inserting the above elements directly into a viral genome. In a preferred embodiment of the invention a baculovirus transfer plasmid, which is later used to produce a recombinant baculovirus, is modified to contain the elements listed above. A DNA segment including at least a portion of the gene to be inhibited is inserted into the DNA region (4) above to produce an expression unit capable of directing synthesis of sense and antisense RNA molecules corresponding to the gene.

Thus after insertion of the DNA segment the elements of the expression unit are positioned in the following order:

(1) Enhancer
(2) Promoter
(3) Transcriptional terminator
(4) DNA segment
(5) Transcriptional terminator
(6) Promoter
(7) Enhancer Transcription proceeds in a left-to-right fashion from promoter (2) and terminates at transcriptional terminator (5). Similarly, transcription proceeds in a right-to-left fashion from promoter (6) and terminates at transcriptional terminator (3). Thus sense and antisense transcripts corresponding to DNA segment (4) are transcribed. Through complementary base pairing these molecules form dsRNA.

One skilled in the art will recognize that the transcriptional terminators can alternatively be positioned upstream from (i.e., to the left of) enhancer (1) and downstream from (i.e., to the right of) enhancer (7).

As discussed in more detail below, a DNA segment for use in the invention can contain sequences from more than one gene, thus allowing an expression vector of the present invention to inhibit expression of multiple genes. One skilled in the art will readily appreciate that segments of DNA whose sequence corresponds to that present in different genes can be combined into a single composite DNA segment for insertion between the enhancer/promoter/terminator sequences of the present invention. Alternatively, a plasmid of the present invention already containing at least one DNA segment can be modified by the sequential insertion of additional DNA segments between the enhancer/promoter/terminator sequences. In a pest control agent of the present invention designed for the inhibition of multiple genes, the genes to be inhibited can come from the same pest species in order to enhance the effectiveness of the pest control agent. In certain embodiments, some or all of the genes can come from different pests in order to broaden the range of pests against which the agent is effective.

In the present invention the expression unit can be created using enhancers and promoters derived from any virus that is capable of entering insect cells. In a preferred embodiment of the invention the viral elements are derived from a baculovirus. In a particularly preferred embodiment the baculovirus is the *Autographa californica* multiple nuclear polyhedrosis virus (AcMNPV), and the promoters and enhancers are derived from this virus.

As mentioned above, one drawback of current baculovirus insecticides is the length of time between application of the insecticide and cessation of larval feeding. In the practice of the present invention it may be desirable, therefore, to minimize the length of time between viral entry into insect cells and transcription of the dsRNA. So that this may be achieved, in a preferred embodiment of the invention the promoter is an immediate early or early viral promoter, and the enhancer is one that functions together with such a promoter. When the virus is the AcMNPV, the promoter is preferably the AcMNPV IE1 promoter, and the enhancer is preferably the AcMNPV hr5 enhancer.

Although in a preferred embodiment of the invention the virus is AcMNPV, the promoter is IE1, and the enhancer is hr5, one skilled in the art will recognize that many alternative embodiments are possible. Many other baculovirus species are known, and immediate early or early promoters and enhancers found in these viruses can be employed. Other baculovirus species include, for example, the *Orgyia pseudotsugata* MNPV, the *Lymantria dispar* MNPV, and the *Bombyx mori* NPV. Although IE1 and hr5 are well characterized AcMNPV-genetic control elements, other immediate early or early gene promoters and enhancers from AcMNPV could be employed in the present invention. Examples of other AcMNPV immediate early of early promoters include those for the p35, gp64, ie-2, 39K, and p143 genes. Examples of other AcMNPV transcriptional enhancers include hr1, hr1a, hr2, hr3, hr4a, hr4b, and hr4c. Of course immediate early and early promoters as well as enhancer elements exist in other baculovirus species, and one skilled in the art will be able to select appropriate genetic elements for use in the present invention when employing these viruses. In a preferred embodiment the SV40 transcriptional terminator, which is known to function efficiently in eukaryotic cells including insect cells, is employed. However other terminators may alternatively be utilized, for example the mammalian β-globin terminator. In certain embodiments of the invention, e.g., if a late viral promoter is used, a viral transcriptional terminator may be employed, for example the 3' UTR of the BV polyhedrin gene (Westwood, J. et al., Analyses of alternative poly(A) signals for use in baculovirus expression vectors, *Virology*, 195:90, 1993).

In addition to baculoviruses, other viruses capable of entering insect cells can also be employed according to the present invention, and appropriate promoters and enhancers selected. Examples of viruses that might be utilized include entomopoxviruses (EPV), in particular group B entomopoxviruses such as *Amsacta moorei* EPV (Li, Y. et al., *J. Virol.*, 71(12): 9557–9562, 1997), densoviruses, in particular *Aedes aegypti* densovirus (Afanasiev, B., *Exp. Parasitol.*, 79(3): 322–39, 1994), nudiviruses, and nodaviruses, e.g., black beetle virus (Ball, L. and Johnson, K., Nodaviruses of Insects, in Miller, L. and Ball, L. (eds.), *The Insect Viruses*, Plenum Press, New York, 1998). Additional viruses of use in the present invention include viruses that infect a broad range of arthropods. Such viruses include white spot shrimp virus (Kanchanaphum, P., et al., *Dis. Aquat. Organ.*, 34(1):1–7, 1998) and baculoviruses of marine shrimp, PmSNPV and PvSNPV (Bonami, J., et al., *J. Struct. Biol.*, 120(2): 134–45). One skilled in the art will be able to select appropriate genetic control elements from these viruses for use in the present invention.

In the case of a baculovirus system the unit is constructed by modifying a baculovirus transfer plasmid (See, e.g., Jarvis, D., "Baculovirus Expression Vectors" in Miller, L. (ed.) *"The Baculoviruses"*; U.S. Pat. No. 5,162,222; Novagen Technical Bulletin TB216, Novagen, Inc. September 1998, all of which are incorporated herein by reference.) to contain the genetic elements recited in parts 1 to 7 above. The DNA segment is inserted between the two promoter/terminator/enhancer complexes to produce a complete expression unit capable of directing synthesis of sense and antisense RNA. The modified transfer plasmid is then utilized to introduce the expression unit into the baculovirus genome.

Methods for modifying the baculovirus genome using transfer plasmids and for selecting baculovirus recombinants are well known in the art. The transfer plasmid containing genetic elements (1) through (7) is cotransfected into insect cells together with linearized baculovirus DNA to construct the recombinant baculovirus. The transfer plasmid contains upstream and downstream segments of baculovirus DNA flanking elements (1) through (7). These segments undergo homologous recombination with the corresponding baculoviral DNA sequences during viral replication. This recombination introduces elements (1) through (7) into the baculovirus genome at a specific locus. Thus the genome of the recombinant baculovirus includes elements (1) through (7), and introduction of the recombinant virus into an appropriate host cell will result in synthesis of dsRNA.

Methods for identifying recombinant baculoviruses are well known in the art and will be described further in the Examples. Likewise, methods for obtaining a homogeneous population of recombinant baculoviruses and generating viral seed stocks and high titer viral stocks are well known in the art. Detailed discussions of these methods may be found, for example, in O'Reilly et al., *Baculovirus Expression Vectors; A Laboratory Manual*, New York: 1992; Richardson, Christopher D. (ed.), *Baculovirus Expression Protocols*—Methods in Molecular Biology, Vol. 39, Totowa, N.J., 1998; Novagen Technical Bulletin TB216, Novagen, Inc. September 1998. The contents of the first two of these three publications are incorporated herein by reference.

Figure 2A:
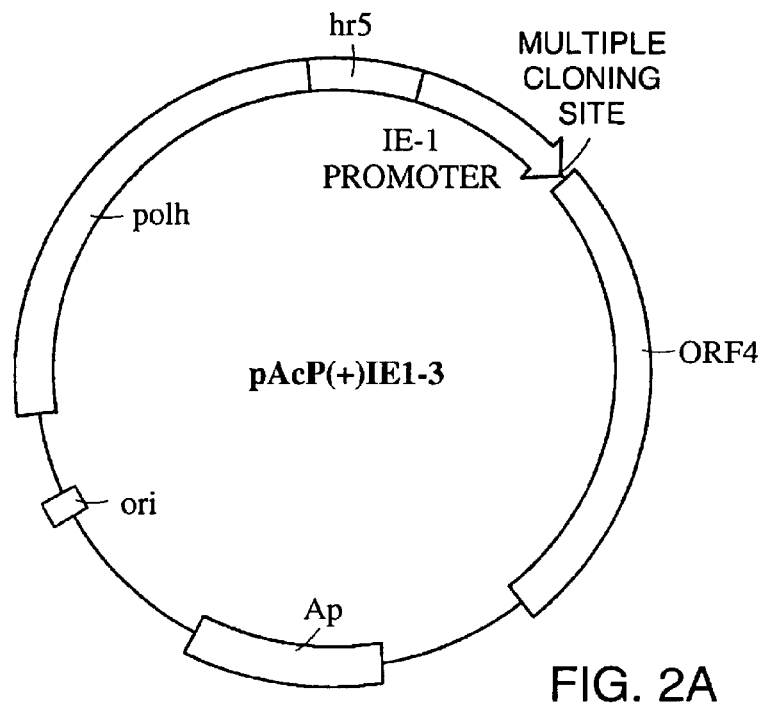
FIG. 2 (Parts A–B) is a diagram of the unmodified baculovirus transfer plasmids pAcP(+)IE1-3 and pAcP(−)IE1-6.
Figure 2B:
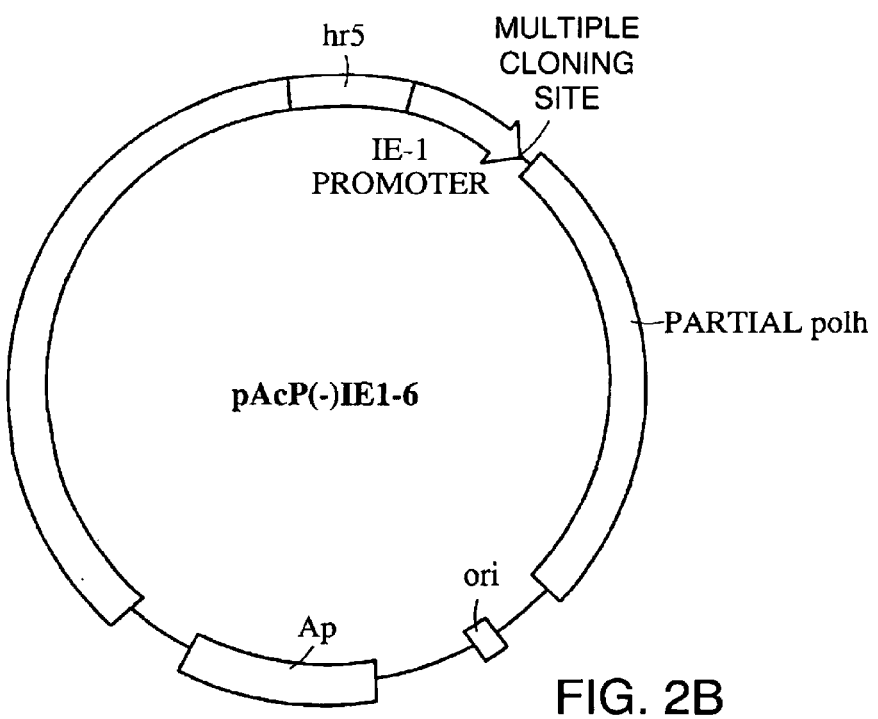

FIG. 2 shows a diagram of unmodified baculovirus transfer plasmids pAcP(+)IE1-3 and pAcP(−)IE1-6 that are employed in certain preferred embodiments of the present invention. The transfer plasmids contain genetic control elements hr5 and IE1 located upstream from a multiple cloning site for insertion of exogenous DNA. The hr5 enhancer, IE1 promoter, and multiple cloning site are targeted for insertion into the polyhedrin gene region of the parental viral genome by long flanking sequences derived from that region. pAcP(+)IE1-3, which contains an intact polyhedrin gene, produces occlusion-positive recombinants when cotransfected into insect cells with appropriate genomic DNA from an occlusion-negative parental virus (e.g., a virus lacking an intact polyhedrin gene). pAcP(−)IE1-6 lacks an intact polyhedrin gene and therefore produces occlusion-negative recombinants when cotransfected into insect cells with appropriate genomic DNA from an occlusion-negative parental virus.

As described in the Background, occlusions are environmentally stable structures composed primarily of the polyhedrin protein, in which virions are packaged within the host cell. Occlusion-positive viruses are able to form such structures while occlusion-negative viruses cannot. Thus occlusion-negative recombinants are environmentally labile. Occlusion-positive and occlusion-negative viruses are particularly suited to certain uses in the practice of the present invention. For example, the environmentally stable, occlusion-positive viruses are suitable for introduction of virus into insects by the oral route as well as for production of large quantities of virus in cell culture or in insect hosts. Nonoccluded viruses are suitable for injection into insects and for addressing basic questions concerning viral entry into cells and events following viral entry.

Preferred baculovirus genomic DNA for use with either transfer plasmid include BacVector-1000 Triple Cut DNA (Novagen, 1998). The progenitor baculoviruses from which this DNA is prepared have the lacZ gene (coding for β-galactosidase) in place of the AcMNPV polyhedrin gene. Following recombination with a transfer plasmid lacking the lacZ gene, lacZ-negative recombinant viruses are produced. Such recombinants can be readily identified in plaque assays by their lack of blue staining in the presence of the lacZ substrate, X-gal.

One skilled in the art will recognize that various other transfer plasmids containing immediate-early, early, or late promoters and, optionally, enhancers, may be used in the practice of the invention. Likewise, other linear baculovirus DNAs may be employed. One skilled in the art will readily be able to determine whether a particular linear baculovirus DNA is appropriate for cotransfection with a particular transfer plasmid in order to produce a desired recombinant baculovirus. Although the preferred embodiment described herein utilizes transfer plasmids and linearized viral DNA to produce a recombinant virus, the invention is not limited to viruses produced in this manner.

Figure 3A:
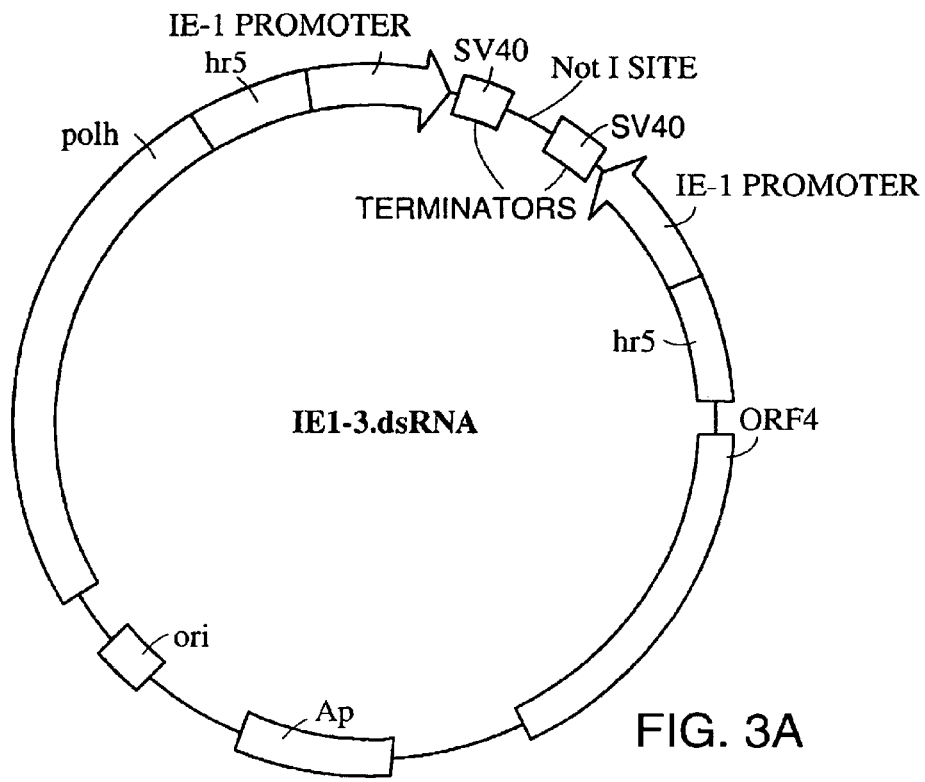
FIG. 3 (Parts A–B) is a diagram of the baculovirus transfer plasmids modified to produce sense and antisense transcripts from an inserted DNA segment, prior to insertion of the DNA segment. These plasmids are referred to as IE1-3.dsRNA and IE1-6.dsRNA.
Figure 3B:
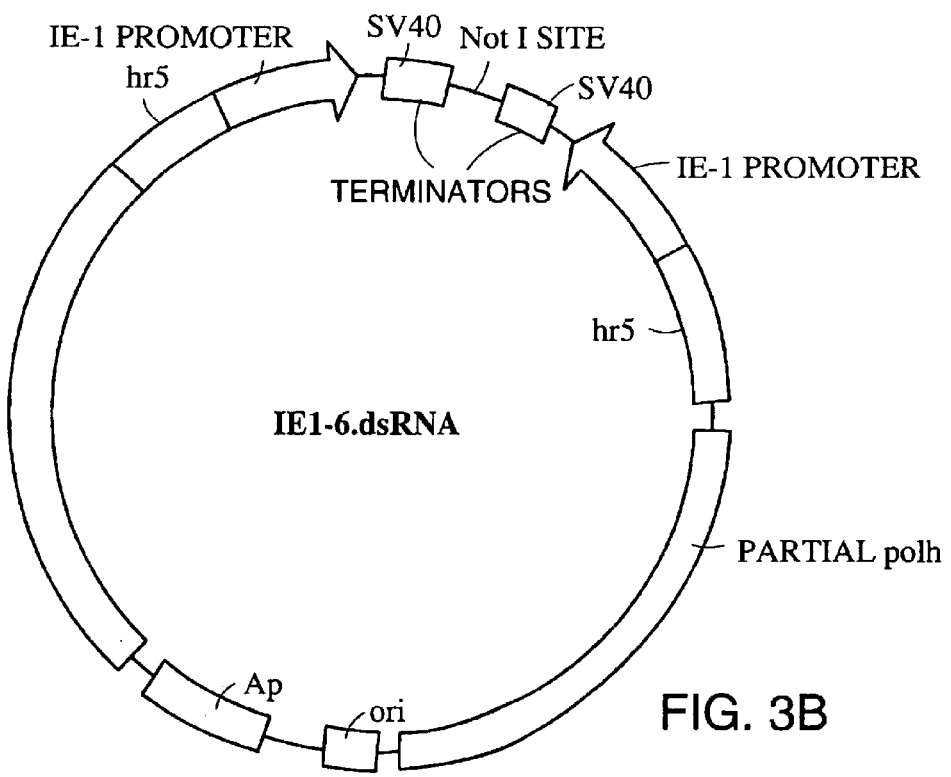
Figure 4A:
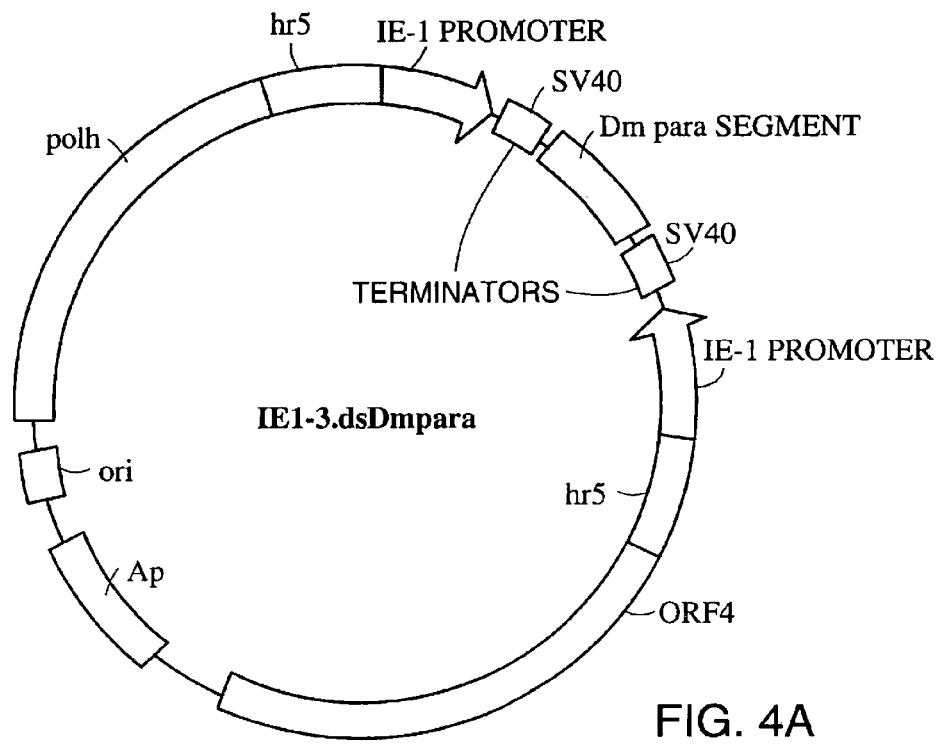
FIG. 4 (Parts A–B) is a diagram of the baculovirus transfer plasmids modified to produce sense and antisense transcripts from an inserted DNA segment corresponding to a portion of the para gene, following insertion of the DNA segment.
Figure 4B:
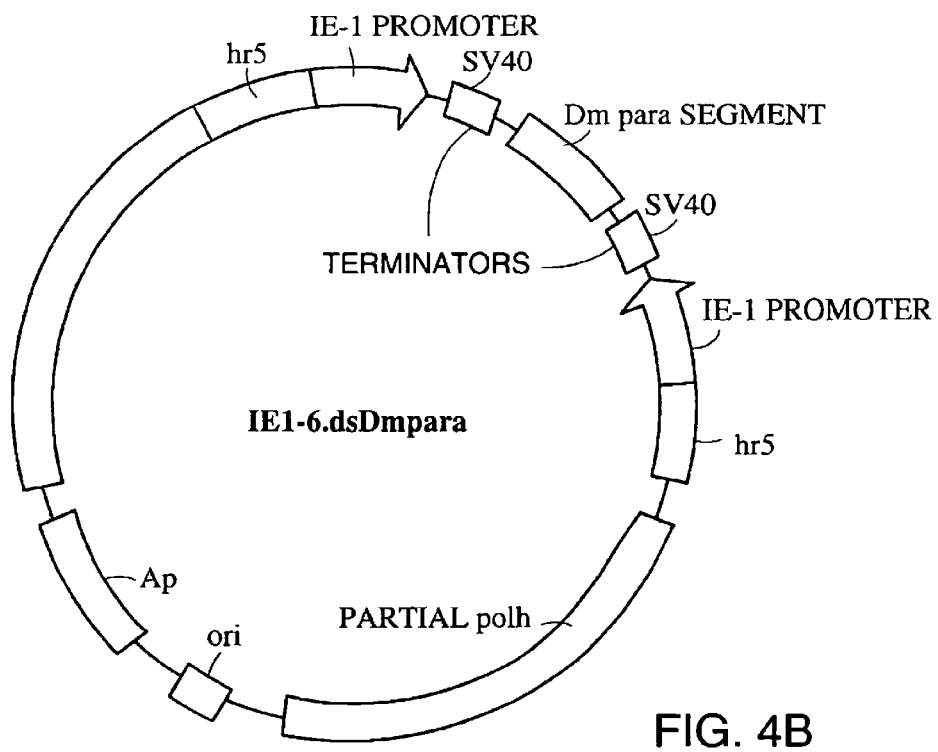

FIG. 3 is a diagram of the baculovirus transfer plasmids modified to produce sense and antisense transcripts from an inserted DNA segment, prior to insertion of the DNA segment. In accordance with the description above, these plasmids contain two copies of the hr5 enhancer/IE1 promoter/SV40 terminator complex in reverse orientation flanking a cloning site for the insertion of a DNA segment. FIG. 4 is a diagram of the baculovirus vectors modified to produce sense and antisense transcripts from an inserted DNA segment, following insertion of a DNA segment containing at least a portion of a target gene. In preferred embodiments of the invention the DNA segment is subcloned into a NotI restriction enzyme site. Since transcription proceeds from both promoters, the DNA insert may be subcloned into the insertion site in either orientation.

Although any insect gene may be inhibited by introducing a recombinant baculovirus of the present invention containing at least a portion of the gene into the insect, certain categories of genes are preferred for different purposes. Within these categories, as described below, certain genes are particularly preferred. For purposes of insect control, a DNA segment of the present invention contains a portion of a gene that encodes an insect protein whose activity is required for the insect to maintain its normal physiological and biochemical functions. Inhibition of expression of the gene significantly impairs feeding, growth, or survival of the insect. Preferred genes include essential genes and genes that play roles in pathways that are targets of existing insecticides.

Many essential genes have been identified during decades of research on *Drosophila*, which serves as a model system for understanding the genetics, biochemistry, and physiology of other insects. Essential genes are characterized by the fact that organisms lacking the gene fail to develop into mature adults, dying as embryos or larvae. Such genes may be required for development or for basic physiological or biochemical processes. Essential genes that are employed in preferred embodiments of the present invention include hunchback, fasciclin II, and the gene encoding the ecdysone receptor (EcR). Hunchback encodes a zinc finger protein involved in patterning the anterior portion of the *Drosophila* embryo. Fasciclin II encodes a cell adhesion molecule essential for proper synaptic development. Ecdysones are steroid hormones that control key steps in molting and metamorphosis through interactions with heteromeric receptors. Null mutations in hunchback, fasciclin II, or EcR lead to an embryonic lethal phenotype in *Drosophila*.

Many existing insecticides affect neurotransmission pathways. Targets for these insecticides include ion channels and enzymes that are involved in the metabolism of neurotransmitters. Thus preferred genes for use in the present invention also include genes whose products play a role in neurotransmission, such as genes encoding ion channels. Such preferred genes include para, one of two genes that encode a pore-forming α subunit of the *Drosophila* voltage-gated sodium channel. Null mutations in para cause embryonic lethality. The voltage-gated sodium channel is the target of a number of widely used chemical insecticides (Zlotkin, E., The insect voltage-gated sodium channel as target of insecticides. *Annu. Rev. Entomol.,* 44: 429–55, 1999).

In certain embodiments it is preferred to select a gene that is expressed in the insect gut, the site where ingested virus enters the insect. Targeting genes expressed in the gut avoids the requirement for the dsRNA and/or the virus to spread within the insect. Preferred gut-expressed genes for use in the present invention include genes that encode protein components of the plasma membrane proton V-ATPase (Dow, J. et al., *J. Exp. Biol.,* 200:237–245, 1997; Wieczorek, H., et al., *J. Bioenerg. Biomemb.,* 31: 67–74 and Dow, J., *J. Bioenerg. Biomemb.,* 31 75–83, 1999). This protein complex is the sole energizer of epithelial ion transport and is responsible for alkalinization of the midgut lumen. The V-ATPase is also expressed in the Malpighian tubule, an outgrowth of the insect hindgut that functions in fluid balance and detoxification of foreign compounds in a manner analogous to a kidney. Specific preferred V-ATPase subunit genes are those encoding subunit B (vha55 in *Drosophila*) and subunit E (vha26 in *Drosophila*). Null mutations in vha55 and vha26 cause embryonic or early larval lethality (Dow, ibid, 75–83, 1999).

For purposes of testing the efficacy of the system in various insect species, genes whose inhibition produces a phenotype that is easy to score are preferred. Inhibiting these genes will not necessarily have a deleterious effect upon the insect but may instead alter a readily detectable characteristic such as eye color. Examples of preferred genes with readily detectable phenotypes include white and Hyperkinetic. White encodes a member of the ATP binding unit (ABC) transporter family of proteins and is involved in transporting pigment precursor molecules into cells. Mutations in white cause *Drosophila* eyes to be white rather than red, as in wild type flies. Hyperkinetic encodes a potassium channel β subunit. Mutations in Hyperkinetic cause repetitive nerve firing and result in an easily detected leg-shaking phenotype in adult flies.

Several additional criteria may be employed in the selection of preferred genes. Preferentially the gene is one whose protein product has a rapid turnover rate, so that dsRNA inhibition will result in a rapid decrease in protein levels. In certain embodiments it is advantageous to select a gene for which a small drop in expression level results in deleterious effects for the insect. For the purpose of conferring specificity, in certain embodiments of the invention it is preferred to select a gene that contains regions that are poorly conserved between individual insect species, or between insects and other organisms. Conversely, if it is desired to target a broad range of insect species it is preferable to select a gene that is highly conserved across these species. In certain embodiments it may be desirable to select a gene that has no known homologs in other organisms.

Although the genes mentioned above have been described primarily in reference to *Drosophila*, of course in the practice of the invention it is preferred to use DNA segments whose sequence exhibits at least 80% identity (and preferably approximately 100% identity) to genes within the pests to be controlled. One such pest is the tobacco hornworm, *Manduca sexta*. Thus, for example, in preferred embodiments of the invention DNA segments with sequences from *Manduca sexta* genes encoding Hunchback, Fasciclin II, Ecdysone receptor, Para, Hyperkinetic, and subunits B and E of the proton V-ATPase are used. These DNA segments are further described in the Examples.

The above description has provided guidelines that govern the selection of preferred genes for use in the practice of the present invention. Frequently a preferred gene may fulfill multiple selection criteria. For example, genes whose products are involved in neurotransmission are frequently essential genes. It is expected that genes whose products are essential, genes whose products are involved in development or neurotransmission, and genes that are expressed in the insect alimentary canal and/or Malpighian tubule will be of most utility in the practice of the present invention. One of ordinary skill in the art will be able to determine, using appropriate techniques, whether a gene falls into one of these categories. Thus the invention is not limited to the specific genes described herein but encompasses any gene whose inhibition exerts a deleterious effect on an insect, including genes that have not yet been characterized by cloning or sequencing.

For many of the insect pests that are potential targets for control by the present invention there is limited information regarding the sequence of most genes or the phenotype resulting from mutation of particular genes. Therefore, selection of appropriate genes from insect pests for use in the present invention may make use of information available from study of the corresponding gene in *Drosophila* or in some other insect species in which the gene has been characterized. Thus, for example, a gene whose null phenotype in *Drosophila* is lethality is a gene of potential utility in the present invention. In some cases it will be possible to obtain the sequence of a corresponding gene from a target insect pest by searching databases such as GenBank using either the name of the gene or the sequence from *Drosophila* or another insect from which the gene has been cloned. Once the sequence is obtained, PCR may be used to amplify an appropriately selected segment of the gene.

However, in many cases the corresponding insect pest gene will not have been cloned. In order to obtain a DNA segment from the corresponding gene in the insect pest species, PCR primers are designed based on the sequence as found in *Drosophila* and/or other insects from which the gene has been cloned. The primers are designed to amplify a DNA segment of sufficient length for use in the present invention. DNA (either genomic DNA or cDNA) is prepared from the insect pest species, and the PCR primers are used to amplify the DNA segment. Amplification conditions are selected so that amplification will occur even if the primers do not exactly match the target sequence. Alternately, the gene (or a portion thereof) may be cloned from a genomic or cDNA library prepared from the insect pest species, using the *Drosophila* (or other cloned insect gene) as a probe. Techniques for performing PCR and cloning from libraries are well known to one skilled in the art. Further details of the process by which DNA segments from target insect pest species may be isolated based on the sequence of genes previously cloned from other insect species are provided in the Examples. One of ordinary skill in the art will recognize that a variety of techniques may be used to isolate gene segments from insect pest species that correspond to genes previously isolated from other species.

A DNA segment for use in the present invention is preferably greater than about 50 to 100 nucleotides and less than about 2000 nucleotides in length. More preferably the DNA segment is several hundred nucleotides in length. The DNA segment preferably contains substantially sequences that appear in the mature mRNA corresponding to the target gene. Although the DNA segment may contain intron or promoter sequences, in preferred embodiments such sequences constitute less than about 10% of the DNA segment.

Preferably the dsRNA exhibits a substantial degree of sequence identity with the target gene. Greater than 90% or even 100% identity between the sequence of the dsRNA and the gene to be inhibited is preferable. Sequences less than about 80% identical to the target gene are substantially less effective. Thus inhibition is specific to the gene whose sequence corresponds to the dsRNA. Expression of unrelated genes is not affected. This specificity allows the invention to selectively target pest species while having minimal effects on other organisms exposed to the invention.

In certain preferred embodiments of the invention the DNA segment comprises a linked set of individual DNA segments (referred to herein as DNA subsegments), each DNA subsegment containing a portion of a different gene or different portions of the same gene. Such a DNA segment comprised of multiple DNA subsegments is referred to herein as a composite DNA segment. (In general, unless otherwise specified, a DNA segment can refer to either a composite DNA segment or a DNA subsegment.) In general, the DNA subsegments may be present in either orientation with respect to one another. In a preferred embodiment of the invention each promoter directs transcription of a composite RNA comprising sequences corresponding to each subsegment. Thus both sense and antisense RNA corresponding to each subsegment are produced. Complementary base pairing to form dsRNA can occur by pairing of any portion of the RNA with its complement.

Each subsegment preferably meets the length and sequence criteria described above with respect to its corresponding gene, i.e., each subsegment is preferably several hundred nucleotides in length, and each subsegment preferably contains substantially sequences that appear in the mature mRNA corresponding to the target gene for that subsegment (as opposed to intron sequences or other non-coding sequences). Each subsegment preferably exhibits a substantial degree of sequence identity with its gene target. Thus, although when taken as a whole, a composite DNA segment may not satisfy the length and sequence criteria described above with respect to the target genes corresponding to each subsegment, in a preferred embodiment each DNA subsegment when considered alone does satisfy the length and sequence criteria with respect to its corresponding target gene.

By way of illustration, as shown in FIG. 5A, in a particular embodiment a composite DNA segment includes a DNA subsegment containing sequences from the para gene, a DNA subsegment containing sequences from the Hk gene, and a DNA subsegment containing sequences from the vha55 gene. Each subsegment meets the length, sequence, and identity criteria described above with respect to its target gene. Transcription directed by promoter 1 yields a transcript that can hybridize to each of three complementary regions in the transcript directed by promoter 2, yielding a product with three dsRNA regions as shown in FIG. 5B. Each double-stranded region is able to inhibit its corresponding gene. Thus in this embodiment a single vector directs synthesis of dsRNA able to inhibit three different target genes.

Inhibition of gene expression may be quantified by measuring either the endogenous target RNA or the protein produced by translation of the target RNA. Techniques for quantifying RNA and proteins are well known to one of ordinary skill in the art. In certain preferred embodiments gene expression is inhibited by at least 10%, preferably by at least 33%, more preferably by at least 50%, and yet more preferably by at least 80%. In particularly preferred embodiments of the invention gene expression is inhibited by at least 90%, more preferably by at least 95%, or by at least 99% within cells in the pest organism. In preferred embodiments of the invention inhibition occurs rapidly after the pest organism comes into contact with the virus. In preferred embodiments significant inhibition of gene expression occurs within 24 hours after the insect comes into contact with the virus. In more preferred embodiments significant inhibition occurs within 12 hours after the insect comes into contact with the virus. In yet more preferred embodiments significant inhibition occurs between 6 to 12 hours after the insect comes into contact with the virus. In yet more preferred embodiments significant inhibition occurs within less than 6 hours after the insect comes into contact with the virus. By significant inhibition is meant sufficient inhibition to result in a detectable phenotype (e.g., cessation of larval growth, paralysis, etc.) or a detectable decrease in RNA and/or protein corresponding to the gene being inhibited. Note that although in certain embodiments of the invention inhibition occurs in substantially all cells of the insect, in other preferred embodiments inhibition occurs in only a subset of cells expressing the gene. For example, if the gene to be inhibited plays an essential role in cells in the insect alimentary tract, inhibition of the gene within these cells is sufficient to exert a deleterious effect on the insect.

In order to achieve inhibition of a target gene selectively within a given species which it is desired to control, the DNA segment preferably exhibits a low degree of sequence identity with corresponding segments in other species. Preferably the degree of identity is less than approximately 80%. Still more preferably the degree of identity is less than approximately 70%. Yet more preferably the degree of identity is less than approximately 50%. Untranslated regions (UTRs), i.e., 5' and 3' UTRs, frequently display a low degree of conservation across species since they are not constrained by the necessity of coding for a functional protein. Thus in certain preferred embodiments the gene portion consists of or includes a UTR. In other preferred embodiments of the invention the gene segment contains an exon that is not found in insect species for which control is not desired. Conversely, if it is desired to inhibit a target gene within a number of different species which it is desired to control, the DNA segment preferably exhibits a high degree of identity with the corresponding segments in these species and a low degree of identity with corresponding segments in other species, particularly in mammals. Although, as mentioned above, it is highly unlikely that dsRNA inhibition operates in mammalian cells, the ability to select gene regions that exhibit low degrees of identity across species affords an additional measure of safety.

Selection of appropriate gene segments is facilitated by using computer programs that automatically align DNA sequences and indicate regions of identity or homology. Such programs are used to compare gene sequences obtained, for example, by searching databases such as GenBank or by sequencing PCR products. Comparison of genes from a range of insect species allows the selection of gene segments that display an appropriate degree of identity between species. In the case of genes that have not been sequenced, e.g., genes either from insect pests or other insects, Southern blots are performed to allow a determination of the degree of identity between genes in target insect species and other insects. By performing Southern blots at varying degrees of stringency, as is well known in the art, it is possible to obtain an approximate measure of identity. These procedures allow the selection of DNA segments that exhibit a high degree of identity to target genes in insects to be controlled and a lower degree of identity to corresponding genes in other insects, e.g., beneficial insects which it is desired to protect.

One skilled in the art will realize that there is considerable latitude in selecting appropriate regions of genes for use in the present invention. Without intending to limit the scope of the invention, the Examples specifically identify portions of genes that are employed in certain preferred embodiments of the invention.

In certain preferred embodiments of the present invention a productive viral infection need not be established for the insect control agent to be effective. As long as the virus can enter the cells, transcription from early viral promoters can occur even in insects that the virus cannot productively infect. For example, reporter genes operably linked to AcMNPV early promoters can be expressed in cell lines derived from *Drosophila* and mosquito (Carbonell L., et al., Baculovirus-mediated expression of bacterial genes in dipteran and mammalian cells, *J. Virol.*, 56:153, 1985 and Morris, T and Miller, L., Promoter influence on baculovirus-mediated gene expression in permissive and non-permissive insect cell lines, *J. Virol.*, 66:7397, 1992), reviewed in Miller, L. and Lu, A., "Baculovirus Host Range" in *The Baculoviruses*, New York, 1997. According to Miller and Lu, "The ability of AcMNPV (a baculovirus) to express genes under insect or early (viral) promoter control in these different cell lines indicates that the AcMNPV can adsorb, penetrate, uncoat, and present its DNA in an expressible form in the nucleus of a diverse range of insect cells."

The IE1 promoter is active in a variety of cell types in which BV cannot establish a productive infection including *Drosophila* and mosquito cell lines (Shotkoski et al., *FEBS Letters* 380: 257, 1996; Harper, PhD thesis, University of Wisconsin, Madison, 1995). This synthesis of dsRNA and associated anti-insect activity does not require productive viral infection. Transcription from the IE1 promoter initiates within the first 15 to 30 minutes after viral entry (Chisholm, G. E. and Henner, D. J., Multiple early transcripts and splicing of the *Autographa californica* nuclear polyhedrosis virus IE-1 gene, *J. Virol.*, 62:3193, 1988; Guarino L. A. and Summers, M. D., Nucleotide sequence and temporal expression of a baculovirus regulatory gene, *J. Virol.*, 61: 2091, 1987). Viral gene products have been detected as soon as 30 minutes after inoculation. Most prior art recombinant BV insect control agents that express heterologous genes do so from a late viral promoter. Thus in prior art BV insect control agents high level expression does not begin until a late stage of the viral replicative cycle, many hours after viral entry.

The low levels of dsRNA required for gene inhibition and the fact that dsRNA can spread within the target organism imply that the BV insecticides provided by this invention will be effective against insects in which BV cannot establish a productive infection. This feature may circumvent one limitation of prior art BV insecticides, namely the necessity of utilizing different species of BV to target different insect pests. In addition, the potency of dsRNA means that a target insect will only need to ingest a small number of viruses to be affected. Although any insect may be selected as a target, in certain embodiments of the invention preferred target insects include the cotton bollworm (*Helicoverpa zea*), the cabbage looper (*Trichoplusia ni*), the alfalfa looper (*Autographa californica*), the tobacco hornworm (*Manduca sexta*), the tobacco budworm (*Heliothis virescens*), the fall armyworm (*Spodoptera frugiperda*), the European corn borer (*Ostrinia nubilalis*), the eastern spruce budworm (*Choristoneura fumiferana*), the western spruce budworm (*C. occidentalis*), and the gypsy moth (*Lymantria dispar*).

A major drawback of chemical pesticides is their toxicity towards non-pest insects and other organisms. The BV insect control agent described herein provides selectivity in two ways that will minimize effects on non-target insects and other organisms. First, the present invention can be used to inhibit genes that are found only in insects. Organisms lacking these genes will be unaffected by exposure to the BV. Selectivity is also achieved by the synthesis of dsRNA corresponding to gene segments that exhibit a high degree of homology among insect species to be inhibited relative to the degree of homology with non-target insects and other organisms. Since dsRNA inhibition requires dsRNA with a high degree of homology between the dsRNA and the gene to be inhibited (preferably greater than 80% identity), selection of regions with low inter-species conservation will minimize effects on non-target species.

Methods for producing baculovirus in quantities sufficient for research, field trials and commercial applications are well known in the art. Baculoviruses may be produced using either in vitro or in vivo methods (See Black, et al., 1997 for an overview of these methods). In vitro methods refer to the production of BV in tissue culture cells, i.e., in insect cell lines such as SF9 (See Weiss, S. and Vaughan, J., Cell culture methods for large-scale propagation of baculoviruses, in: *The Biology of Baculoviruses* (Granados, R. and Federici, B., eds.), Vol. II, pp. 63–87, CRC Press, Boca Raton, Fla. for an extensive review of in vitro methods). Preferably the cell line is adapted to growth in serum free medium. The cells are infected with a viral seed stock, preferably a stock exhibiting genetic stability and capable of yielding high titers of virus (e.g. $10^8$ plaque forming units/ml). For large scale production (i.e. greater than 10,000 liters) as is needed for commercial applications, stir-tank bioreactors rather than containers such as spinner bottles, roller bottles, or shaker culture are preferable. In vivo production refers to the growth of BV in whole insects and therefore requires that the insect be one in which the virus can establish a productive infection (See In vivo production of baculoviruses, in: *The Biology of Baculoviruses* (Granados, R. and Federici, B., eds.), Vol. II, pp. 31–61, CRC Press, Boca Raton, Fla. for an extensive review of in vivo methods.) In vitro production methods are generally preferred both for small scale production of BV and for large scale production of recombinant BV.

Figures 6, 7:
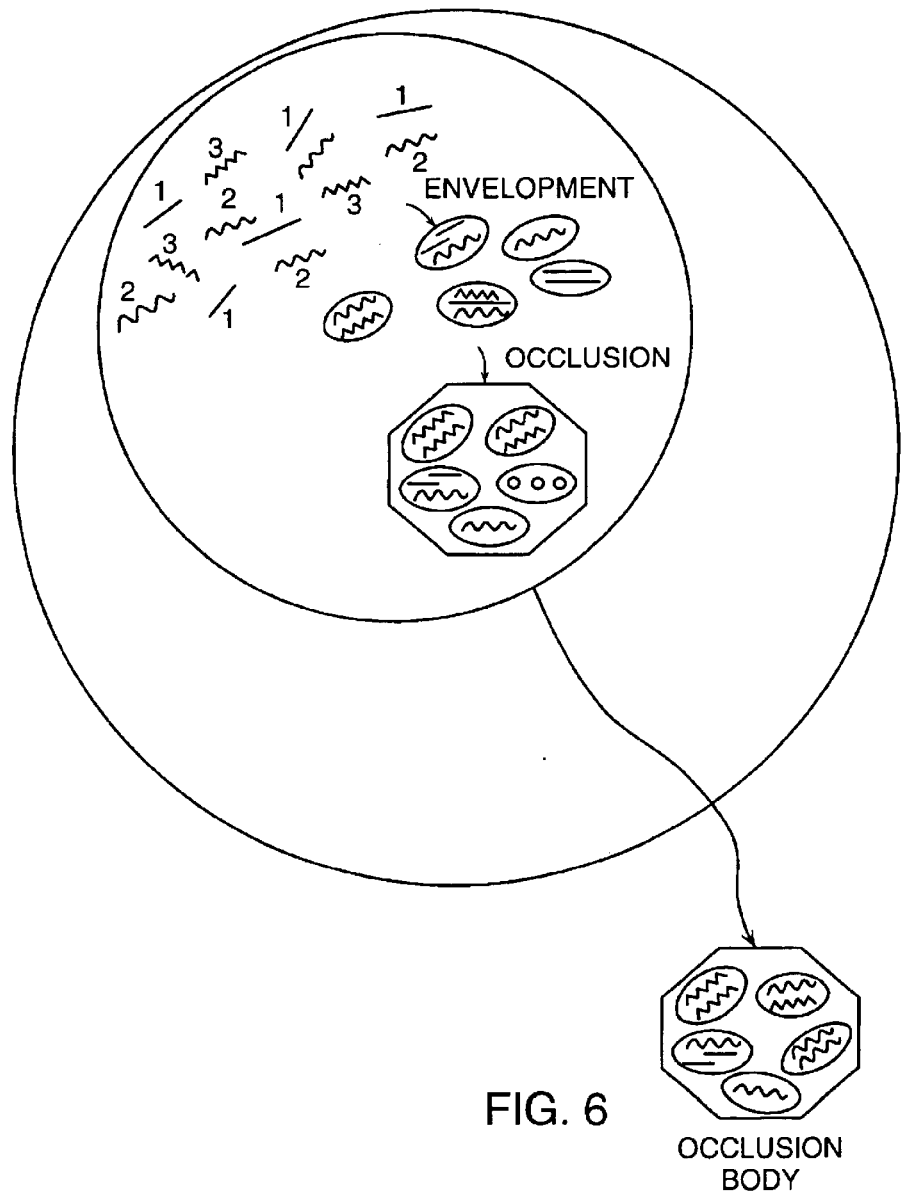
FIG. 6 is a diagram illustrating the packaging of multiple different recombinant viruses into a single occlusion body.
FIG. 7 is the sequence of the SV40 transcriptional terminator.

One skilled in the art will recognize that in the case of production of occluded virus, it is possible to produce occlusion bodies containing more than one species of recombinant virus by coinfecting insects or insect cell lines with multiple different recombinant viruses (discussed in Wood, H. and Granados, R. Genetically Engineered Baculoviruses as Agents for Pest Control, *Annu. Rev. Microbiol.,* 45:69–87, 1991). In the present invention, the genome of each of these recombinant viruses contains genetic elements to direct synthesis of dsRNA to inhibit one or more genes in a pest to be controlled. During the course of infection of the insect or insect cell line used to produce the pest control agent, viral genomes are synthesized and packaged into virions. In the case of MMPVs (but not NPVs) these virions are ultimately packaged at random into occlusion bodies. Thus a given occlusion body will likely contain more than one different recombinant virus. For example, FIG. 6 shows a cell that has been infected with three different recombinant viruses of the present invention, each designed to inhibit expression of the para gene in a different insect species. Virus 1 contains a portion of the *Heliothis virescens* para gene; Virus 2 contains a portion of the *Helicoverpa zea* (cotton bollworm) para gene, and Virus 3 contains a portion of the *Trichoplusia ni* (cabbage looper) para gene. The occlusion bodies produced in this cell contain multiple copies of all three viruses, as shown in FIG. 6. It will be appreciated that the presence within the occlusion body of multiple different viruses, designed to inhibit different genes (either the same gene in different species or different genes in a single species, or any combination of these), will enhance the effectiveness of the pest control agent against a given pest or will broaden the range of pests against which the pest control agent acts.

For use as an insecticide the baculovirus may be formulated in any of a number of ways well known in the art. Methods and considerations involved in the preparation of baculovirus insecticides for field trials and commercial applications are found in Black, et al, 1997 and in U.S. Pat. No. 5,858,353, which is incorporated herein by reference in its entirety. In general, a preferred formulation will protect the virus from environmental degradation, allowing time for the virus to be ingested by the target insect. A preferred formulation should not contain any ingredients that are detrimental to plants or adversely affect insect feeding behavior. Preferably the formulation is as a flowable or a wettable powder compatible with conventional spray equipment. The insecticidal agent is preferably combined with an agriculturally suitable carrier, e.g., a liquid such as water, alcohol, or other organic solvents or oils, or a powder such as talc, clay, or other silicate. The formulated product may contain a variety of components including gustatory stimulants, thickening agents, UV screening agents, optical brighteners, viral synergists, and agents to enhance spreading and sticking to plant surfaces in addition to the virus itself. The virus may be administered with low levels of conventional insecticides, which may provide cost-effective insect control without the use of large quantities of chemicals.

Other Embodiments

The foregoing paragraphs have described a preferred embodiment in which separate sense and antisense RNA molecules are synthesized and dsRNA is produced through intermolecular hybridization of complementary sequences. As those skilled in the art will readily appreciate, dsRNA can also be produced through intramolecular hybridization of complementary regions within a single RNA molecule. An expression unit for synthesis of such a molecule comprises the following elements, positioned from left to right:

1. A DNA region comprising a viral enhancer.
2. A DNA region comprising an immediate early or early viral promoter oriented in a 5' to 3' direction so that a DNA segment inserted into the region of part 4 is transcribed.
3. A DNA region into which a DNA segment can be inserted. Preferably this region contains at least one restriction enzyme site.
4. A DNA region comprising a transcriptional terminator arranged in a 5' to 3' orientation so that a transcript synthesized in a left to right direction from the promoter of part 2 is terminated.

A DNA segment comprising a portion of the gene to be inhibited and a substantially identical DNA segment in reverse orientation are inserted into the region of part 3 to produce an expression unit capable of directing synthesis of an RNA molecules comprising sense and antisense sequences. Through intramolecular complementary base pairing this molecule forms dsRNA. In a preferred embodiment of this second type of expression unit, the promoter is the IE-1 promoter, the enhancer is the hr5 enhancer, the transcriptional terminator is the SV40 terminator, and the expression unit is created by modifying a baculovirus transfer plasmid. The transfer plasmid is then cotransfected into insect cells with linear baculovirus DNA to produce a recombinant baculovirus whose genome includes the expression unit, as described in the previous section.

In some embodiments, rather than using a baculovirus transfer plasmid containing the hr5 enhancer/IE-1 promoter/SV40 terminator complex it may be preferable to use alternative promoters such as the polyhedrin promoter. The polyhedrin promoter is a very late promoter and directs extremely high levels of transcription relative to other baculovirus promoters. Although in most embodiments of the invention it is preferred to employ an early promoter, there may be situations in which the high level of expression achievable with the polyhedrin promoter is desired. It is frequently the case that the amount of damage done by the adult form of an insect is of minimal or no concern compared with the amount of damage caused by larvae. In such a situation it may be desired to contact insects with the recombinant virus with the goal of inhibiting expression of genes within the progeny. For this purpose it may be more important to achieve high levels of expression of dsRNA or to achieve expression late in the infection cycle than to achieve rapid expression. Thus in certain preferred embodiments of the invention a late promoter such as the polyhedrin or p10 promoter is employed.

It is noted that the invention is not limited to the embodiments described herein and the examples presented below and that various changes and modifications may be made by those of ordinary skill in the art without departing from the scope and spirit of the appended claims.

EXAMPLES

Sequences of primers referred to in these examples are presented in FIG. 8.

Example 1

Construction of Baculovirus Transfer Plasmids for Expression of dsRNA

Baculovirus transfer plasmids pAcP(+)IE1-3 and pAcP(−)IE1-6 were obtained from Novagen, Inc., 601 Science Drive, Madison, Wis., 53711. For cloning into pAcP(-)IE1-3, the SV40 transcriptional terminator (FIG. 7, SEQ ID NO:1) was amplified using the primers 5'-SV40Xba (SEQ ID NO:2) and 3'-SV40Sac (SEQ ID NO:3). The 5' and 3' primers contain an XbaI and a SacII restriction site respectively at their 5' ends. The amplified fragment was subcloned into the XbaI and BamHI sites of pAcP(-)IE1-3 to create plasmid IE1-3-SV40. For cloning into pAcP(-)IE1-6, the SV40 transcriptional terminator was amplified using the primers 5'-SV40Xba (SEQ ID NO:2) and 3'-SV40Bam (SEQ ID NO:4). The 5' and 3' primers contain an XbaI and a BamHI restriction site respectively at their 5' ends. The amplified fragment was subcloned into the XbaI and BamHI sites of pAcP(-)IE1-6 to create plasmid IE1-6-SV40.

Plasmids IE1-3-SV40 and IE1-6-SV40 contain an hr5 enhancer/IE1 promoter/SV40 terminator complex (with the SV40 terminator in opposite orientation with respect to hr5 and IE1). PCR amplification of the hr5 enhancer/IE1 promoter/SV40 terminator complex was performed using the original 5'SV40Xba primer as the 3' primer and either primer IE1-3.5' (SEQ ID NO:5) or IE1-6.5' (SEQ ID NO:6) as the 5' primer, for amplification from plasmids IE1-3-SV40 and IE1-6-SV40 respectively. Primers IE1-3.5' and IE1-6.5' are plasmid-specific primers designed based on the extreme 5' end of the hr5 region of the respective plasmids, with novel restriction sites engineered into the 5' ends. IE1-3.5' contains an SpeI site at the 5'end, and IE1-6.5' contains a BglII site at the 5' end. The amplified hr5 enhancer/IE1 promoter/SV40 terminator complexes were subcloned into the PCR cloning vector PCR2.1 (Invitrogen, 1600 Faraday Ave., Carlsbad, Calif., 92008) between the 3' overhangs, according to the manufacturer's instructions, to create plasmids 2.1IE1-3 and 2.1IE1-6 wherein 2.1IE1-3 contains the hr5/IE-1/SV40 complex amplified from plasmid IE1-3-SV40, and 2.1IE1-6 contains the hr5/IE-1/SV40 complex amplified from plasmid IE1-6-SV40.

The hr5/IE1/SV40 complex was isolated from plasmid 2.1IE1-3as an SpeI-XbaI fragment and subcloned into the XbaI site of IE1-3-SV40, taking advantage of the fact that SpeI and XbaI have compatible "sticky ends". The resulting plasmid, referred to as IE1-3.dsRNA, contains two copies of the hr5/IE1/SV40 complex in opposite orientation flanking a small portion of the pAcP(+)IE1-3 multiple cloning site.

The hr5/IE1/SV40 complex was isolated from plasmid 2.1IE1-6 and subcloned into IE1-6-SV40 as follows: Plasmid IE1-6-SV40 was digested with PstI, blunted with T4 polymerase, and then digested with BglII. Plasmid 2.1IE1-6 was digested with XbaI and then blunt-ended using Klenow enzyme. The plasmid was then cut with BglII, and the hr5/IE1/SV40 complex was subcloned into the IE1-6-SV40 backbone to create plasmid IE1-6.dsRNA.

Due to the fact that the XbaI restriction site present at the 5' end of the SV40 terminator is blocked by Dam methylation, an XbaI site present in the PCR2.1 multiple cloning site was utilized to remove the hr5/IE1/SV40 complex from plasmids 2.1IE1-3 and 2.1IE1-6 as described above. Use of this site resulted in the inclusion of 55 nucleotides of the PCR2.1 multiple cloning site downstream of the hr5/IE1/SV40 complex, thus plasmids IE1-3.dsRNA and IE1-6.dsRNA contain 55 nucleotides of multiple cloning site on the opposite side of the SV40 element from the junction between the IE1 promoter and the SV40 terminator. These 55 nucleotides are presented in FIG. 9 as SEQ ID NO:7.

Example 2

Isolation of DNA Segments from Target Insect Genes

Preparation of cDNA Templates for Amplification of Target Genes

Total RNA was isolated from *Drosophila* and *Manduca* larvae and adults using a standard LiCl/urea precipitation protocol. Crude extracts were extracted with phenol/chloroform, using acidic phenol to extract DNA into the organic phase while leaving RNA in the aqueous phase. First strand cDNA synthesis was performed using the Superscript Preamplification System (Gibco BRL, Cat. 18089011, 1999).

Isolation of DNA Segments from Target Genes

Segments of DNA from the *Drosophila* para, white, vha55, and vha26 genes and the *Manduca* hb, EcR, fasciclinII, vha55, and vha26 genes were amplified from first strand cDNA by PCR using primers designed on the basis of sequences available in GenBank. Standard PCR amplification conditions were used. (Annealing: temperature=55 degrees C., time=45 sec; Extension: temperature=72 degrees C., time=50 sec; Denaturing: temperature=95 degrees C., time=30 sec; Taq polymerase). Thirty-nine rounds of amplification were performed using primers described below.

Dm para (GenBank accession number M32078): A DNA fragment encoding the amino terminal region (nucleotides 72–656 of the open reading frame) of the Dm para gene was amplified using appropriate primers (SEQ ID NO:8=5' primer; SEQ ID NO:9=3' primer). This region encodes the first two and part of the third transmembrane segment in homology domain 1.

Dm Hk (GenBank accession number U23545): A DNA segment 1958 base pairs in length that includes 715 bases of the 5'UTR and the first 1242 bases of the open reading frame of the Dm Hk gene was isolated from Dm cDNA clone HC206 (Chouinard, et al., 1995).

Dm white (GenBank accession number X02974): A DNA segment extending from positions 1504–2041 of the open reading frame of the Dm white gene was amplified from Dm cDNA using appropriate primers (SEQ ID NO:10=5' primer; SEQ ID NO:11=3' primer).

Dm vha55 (GenBank accession number X67839): A DNA segment extending from nucleotides 87–819 downstream of the stop codon (where the first nucleotide after the stop codon is considered the reference nucleotide) of the Dm vha55 gene was amplified from Dm cDNA using appropriate primers (SEQ ID NO:12=5' primer; SEQ ID NO:13=3' primer).

Dm vha26 (GenBank accession number U38951): A DNA segment extending from nucleotides 31–643 downstream of the stop codon (where the first nucleotide after the stop codon is considered the reference nucleotide) of the Dm vha26 gene was amplified from Dm cDNA using appropriate primers (SEQ ID NO:14=5' primer; SEQ ID NO:15=3' primer).

Ms para: The Ms homolog of Dm para (hereafter referred to as Ms para) has not been cloned. However, the sequence of a cDNA corresponding to a para homolog in another Lepidopteran pest, *Heliothis virescens* has been cloned and sequenced (GenBank accession number AF072493). In order to obtain a fragment of the Ms para gene, PCR primers were designed based on the *Heliothis virescens* para sequence. Primers (SEQ ID NO:16=5' primer; SEQ ID NO:17=3' primer), designed to amplify nucleotides 631–1176 of the *Heliothis virescens* para open reading frame, were used to amplify DNA from Ms cDNA.

Ms hunchback (GenBank accession number Z30281 is a partial cDNA): A DNA segment corresponding to the last 565 nucleotides of the open reading frame of the Ms homolog of Dm hunchback (referred to herein as Ms hb) was amplified using appropriate primers (SEQ ID NO:18=5' primer; SEQ ID NO:19=3' primer).

Ms fasciclinII (GenBank accession number AF103899): A DNA segment extending from nucleotides 662–1321 of the open reading frame of Ms fasciclinII was amplified from Ms cDNA using appropriate primers (SEQ ID NO:20=5' primer; SEQ ID NO:21=3' primer).

Ms ecdysone receptor (GenBank accession number U19812): A 646 nucleotide DNA segment including the last 339 nucleotides of the 5' UTR and the first 307 nucleotides of the open reading frame was amplified from Ms cDNA using appropriate primers (SEQ ID NO:22=5' primer; SEQ ID NO:23=3' primer).

Ms vha55 (GenBank accession number X64354): A DNA segment extending from nucleotides 30–781 downstream of the stop codon (where the first nucleotide after the stop codon is considered the reference nucleotide) of the Ms vha55 gene was amplified from Ms cDNA using appropriate primers (SEQ ID NO:24=5' primer; SEQ ID NO:25=3' primer).

Ms vha26 (GenBank accession number X67131): A DNA segment extending from nucleotides 9–586 downstream of the stop codon (where the first nucleotide after the stop codon is considered the reference nucleotide) of the Ms vha26 gene was amplified from Ms cDNA using appropriate primes (SEQ ID NO:26=5' primer; SEQ ID NO:27=3' primer).

Example 3

Subcloning Target DNA Segments into dsRNA Baculovirus Transfer Plasmids

Segments of target Dm and Ms genes obtained as described above were subcloned into the vector pHSS7, which contains a multiple cloning site flanked by NotI restriction sites, allowing inserts to be easily removed as NotI fragments. NotI fragments containing each DNA segment were then subcloned into the NotI site of modified baculovirus transfer plasmids IE1-3.dsRNA and IE1-6.dsRNA described in Example 1. For clarity, transfer plasmids and the recombinant baculoviruses derived from them are referred to by the name of the gene of which they contain a segment and the species from which the gene was obtained. For example, the term "Dm para transfer plasmid" refers to a transfer plasmid constructed as described herein so as to direct synthesis of dsRNA, i.e., containing a segment of the Dm para gene and flanking genetic control elements. The term "Dm para BV" refers to a recombinant baculovirus derived from a Dm para transfer plasmid.

Example 4

Construction and Isolation of Recombinant Baculoviruses

Recombinant baculoviruses are prepared using Novagen's Direct Plaquing Protocol [Novagen Technical Bulletin TB216 (September 1998)] in which a transfection mixture containing virus DNA, transfer plasmid DNA, and Eufectin Transfection reagent is added to a monolayer of Sf9 cells followed by an agarose overlay. As a backup, a liquid overlay procedure is also performed, which involves incubation of transfected cells under an overlay of liquid medium for 3 days followed by a plaque assay using the supernatant. When using the direct plaquing protocol with plasmids obtained by modification of pAc(-)IE1-6, the plasmids are linearized before transfection in order to increase the yield of recombinants.

Preparation of Transfer Plasmid DNA

Baculovirus transfer plasmids constructed as described in Example 3 are employed together with the Novagen BacVector-1000 Transfection kit to construct recombinant baculoviruses according to the protocol provided in Novagen Technical Bulletin TB216 (September 1998). Briefly, transfection quality plasmid DNA is prepared using a plasmid purification kit obtained from QIAGEN, Inc. (28159 Stanford Avenue, Valencia, Calif. 91355) and resuspended in TlowE (10 mM Tris-HCl, pH 8.0, 0.1 mM EDTA). Plasmids obtained by modification of the pAc(-)PIE1-6 transfer plasmid are linearized by digesting 5 µg of each plasmid with BplI (or an alternative restriction enzyme that has a unique site in the plasmid and has no site in the insert), precipitating digested DNA, and resuspending in 45 µl TlowE.

Cotransfection of Transfer Plasmid DNA and Linearized Viral DNA

For each transfection 1 vial of Ready-Plaque Sf9 cells is thawed and opened as directed, and the contents transferred into a sterile 50 ml polypropylene centrifuge tube. Thirty-nine ml of 28 degree C. Sf-900 II SFM medium (Life Technologies) is added as directed, followed by gentle mixing. For each transfection, one 25 cm$^2$ T-flask and four 60 mm tissue culture Petri dishes are seeded with 6 ml SFM medium containing 3×10$^6$ Sf9 cells, and the cells are allowed to attach for about 20 min at 28 degrees C. after gentle mixing to distribute the cells evenly. The medium is replaced with fresh 28 degree C. medium after approximately 1 hour and washed twice with medium during the incubation step described below.

For each transfection, 100 ng of BacVector-1000 Virus DNA and 500 ng transfer plasmid DNA are combined and diluted to a final volume of 25 µl in medium in a sterile 6 ml polystyrene tube. For each transfection 20 µl of Nuclease-free Water and 5 µl of Eufectin Transfection Reagent are combined in a separate sterile 6 ml polystyrene tube. Each DNA mixture is added to one tube containing water and Eufectin, which is then swirled and incubated at room temperature for 15 min. After the incubation a series of dilutions (1/5, 1/25, 1/125, and 1/625) is made, and 0.1 ml of each dilution is added to one of the previously prepared plates containing Sf9 cells for direct plaquing. Dishes are incubated at room temperature for 1 hr, during which they are rocked twice to increase contact with the transfection mixture and keep the cells moist. The remaining transfection mixture from the 1/5 dilution is added to the cells in the T-flask, which is processed according to the liquid overlay transfection protocol. An agarose overlay is prepared as directed and applied to each plate. Plates are incubated at 28 degrees C. for 3–4 days.

Plaque Identification, Staining, and Purification

Three days after transfection monolayers in each plate are observed to identify plaques. Plaque-containing monolayers are stained for β-galactosidase activity. BacVector-1000 Virus DNA contains the β-galactosidase gene while recombinant virus will lack this gene. Therefore, plaques that display β-galactosidase activity (blue in the presence of the substrate X-gal) originate from residual unlinearized parental virus and are not recombinants. Plaques that do not produce β-galactosidase are expected to originate from recombinant viruses. Several candidate recombinant virus plaques are picked from each monolayer and independently purified by replaquing according to Novagen directions, using an agarose overlay and staining as described above. The supernatant from the liquid overlay transfecticin can be used as a source of virus for infection of additional monolayers of Sf9 cells followed by agarose overlay and isolation of plaques. Plaques obtained from the liquid overlay transfection must go through at least one round of subsequent plaque purification as described in Example 5.

Example 5

Preparation and Analysis of High Titer Virus Stocks

Preparation of High Titer Viral Stocks

For plaques isolated according to the direct plaquing protocol, after one round of plaque purification a seed stock of each recombinant virus is prepared according to Novagen directions. Briefly, virus is eluted from a well isolated plaque and used to infect a monolayer of Sf9 cells growing in a 25 cm$^2$ T-flask. After a one hour incubation at room temperature, cells are incubated at 28 degrees C. until a cytopathic effect is observed (typically 3–5 days). Supernatant, typically containing $10^6$–$10^8$ pfu/ml (plaque forming units/ml) is harvested and used as a seed stock to prepare a higher titer, larger volume master stock. To prepare the high titer stock, 0.5 ml of seed stock is used to infect a 75 cm$^2$ T-flask that has been prepared with 10 ml of medium containing Sf9 cells at $2 \times 10^6$ cells/ml. After a 1 hour incubation at room temperature, the medium is replaced with fresh medium, and the cells are incubated at 28 degrees C. until a cytopathic effect is observed (typically 3–5 days). The medium is harvested into a sterile 15 ml Falcon tube and centrifuged at 1000×g for 5 min. to spin down cells and cellular debris. The supernatant is transferred to a fresh tube and constitutes the master stock of virus. A portion (e.g., 1 ml) of master stock is stored at –70 degrees C. to constitute a backup stock (however, repeated thawing and freezing causes a drop in titer). The remainder is stored at 4 degrees C. The titer is determined by plaque assay. Typical titers are 1–$3 \times 10^9$ pfu/ml.

To obtain high volume stocks, Sf9 cells growing in suspension culture (e.g., 200 ml of medium containing $2 \times 10^6$ cells/ml in a 1 L Erlenmeyer flask) are infected with 0.1–0.2 pfu/cell of the 4 degree C. titered master stock of virus, and incubated with shaking at 28 degrees C. until cytopathic effect is observed (3–5 days). Medium is harvested and centrifuged at 1000×g for 5 min. The supernatant constitutes a high volume stock with a titer typically in the range of 1–$3 \times 10^9$ pfu/ml.

PCR Analysis of Viral Stocks

Virus stocks are analyzed by PCR to confirm that the recombinant viruses contain the DNA segments present in the transfer plasmids used in creation of the viruses. Viral DNA templates are prepared by lysing the virus and treating with Proteinase K as follows. Briefly, 89 $\mu$l lysis buffer (10 mM Tris-HCl, pH 8.3, 100 mg/ml gelatin, 0.45% Triton X-100, 0.45% Tween-20, 50 mM KCl) is combined with 10 $\mu$l high-titer virus stock (>$10^8$ pfu/ml) and 1 $\mu$l Proteinase K (6 mg/ml in H$_2$O) and incubated for 1 hr at 60 degrees C., followed by a 10 min incubation at 95 degrees C. to inactivate Proteinase K. DNA template (typical yield is ~145 pg) is used in a standard PCR assay using primers specific for the DNA segment expected to be present in each recombinant virus (e.g., the primers originally used in the isolation of the DNA segments from insect DNA described in Example 2).

Example 6

Bioassays of Recombinant Baculoviruses in Dm Embryos

High titer virus stocks of Dm para BV, Dm Hk BV, Dm white BV, Dm vha55 BV, and Dm vha26 BV are prepared as described in Example 6. For injection, nonoccluded virus stocks, i.e., those derived from transfer plasmids obtained by modification of pAcP(–)IE1-6, are employed. Injections are performed essentially as described in Misquitta, L. and Paterson, B., *Proc. Natl. Acad. Sci., USA*, 96, 1451–1456, 1999). Briefly, cages containing 2–4 day old wild type *Drosophila* are set up, and eggs are collected in a synchronized fashion (every 30 to 60 min) over a 1–2 day period for injection. Collected eggs are washed and mounted in an anterior to posterior fashion on a glass slide. Eggs are injected in the posterior end, directly through the chorion, slightly off-center. Although injecting eggs in the posterior end, as is performed for P-element transformations, may be most convenient, eggs may be injected anywhere. After injection, eggs are stored in a moist chamber to prevent desiccation. Between 100 and 200 embryos are injected with an appropriate volume of high titer virus stock of the recombinant baculoviruses containing DNA segments corresponding to the Dm para, Hk, white, vha55, and vha26 genes, with an equal volume of high titer wild type virus stock, or with an equal volume of SFM medium. Appropriate volumes range from 0.1 to 1.0 nl. Embryos are allowed to develop, and phenotypes are observed over the course of development to determine the effects of each virus.

Null mutations in para, vha55, or vha26 result in embryonic or early larval lethality. For genes with lethal phenotypes, the effects of a particular virus will be assessed by comparing the survival of embryos injected with that virus with the survival of embryos injected with wild type virus. Injected embryos that survive to develop into larvae are assessed for evidence of deleterious effects or phenotypes caused by the virus. Incomplete inhibition could result in a wide spectrum of effects. Mutations in Hk cause a leg-shaking phenotype in adult flies, thus the effects of the Hk BV are assessed by examining adult flies for leg-shaking behavior. The effects of the recombinant BV containing a portion of white are assessed by examining the eye color of adult flies. A color change from red (wild type) to white indicates activity of the injected white BV. To distinguish effects caused by dsRNA interference with expression of the target gene from effects due to other mechanisms (e.g., effects of viral replication), the phenotype of flies injected with wild type BV is compared with that of flies injected with medium alone.

Example 7

Bioassays of Recombinant Baculoviruses in Dm and Ms Larvae

A series of injections using groups of first, second, third, or fourth instar *D. melanogaster* and *M. sexta* larvae is performed to evaluate the effects of recombinant Dm and Ms BVs. Each group (consisting of at least 5 larvae) is injected with an appropriate volume (e.g., between 1 nl and 20 $\mu$l depending on the size of the larvae at different stages) of either SFM medium, high titer wild type BV virus stock, or high titer virus stock of the recombinant baculoviruses containing DNA segments corresponding to the Dm para, Dm Hk, Dm white, Dm vha55, and Dm vha26 genes (in the case of Dm larvae) or the Ms hb, Ms EcR, Ms fasciclinII, Ms vha55, or Ms vha26 genes (in the case of Ms larvae). Nonoccluded virus stocks, i.e., those derived from transfer plasmids obtained by modification of pAcP(–)IE1-6, are employed in these injection studies. More detailed descriptions of injection procedures are found in Richardson, Christopher D. (ed.), *Baculovirus Expression Protocols—Methods in Molecular Biology*, Vol. 39, Totowa, N.J., 1998, pp. 322–323.

After injection, larvae are examined at 8–12 hour intervals for 5 days. Larvae are assessed for evidence of lethality, pathogenic effects (e.g., defects in molting in the case of larvae injected with EcR BV, defects in neurotransmission in the case of larvae injected with para or fasciclin BV), or decreased feeding. At each observation time, viable and dead larvae are counted. Viable larvae are examined for unusual behaviors or appearance. The ability of larvae to move, to reinvert after being placed on their backs, and to respond to stimulation is determined.

Example 8

Oral Bioassays of Recombinant Baculovirus in *Drosophila melanogaster* and *Manduca sexta*

Polyhedral occlusion bodies are isolated from Sf9 cells infected with occluded BV virus stocks, i.e., those derived from transfer plasmids obtained by modification of pAcP (+)IE1-3. As is well known in the art, centrifugation of infected cells at low speed results in a pellet consisting of virtually pure polyhedra. More detailed protocols are found in Richardson, Christopher D. (ed.), *Baculovirus Expression Protocols*—Methods in Molecular Biology, Vol. 39, Totowa, N.J., 1998. Purified polyhedral occlusion bodies are added to insect diet (either liquid or solid) by mixing a polyhedra-containing suspension with liquid (e.g., sucrose solution for *Drosophila*) or by dropping suspension directly onto the food in the case of solid food. Concentrations of polyhedra ranging from approximately $10^5$/ml to $10^8$/ml are assessed. Groups of larvae at various stages are allowed to feed on the polyhedra-containing food for periods of time ranging from 2 to 24 hours. Larvae are examined at 8–12 hour intervals for 5 days following exposure to polyhedra-containing food. Larvae are assessed for evidence of lethality, pathogenic effects (e.g., defects in molting in the case of larvae exposed to EcR BV, defects in neurotransmission in the case of larvae exposed to para or fasciclin BV), or decreased feeding. At each observation time, viable and dead larvae are counted. Viable larvae are examined for unusual behaviors or appearance. The ability of larvae to move, to reinvert after being placed on their backs, and to respond to stimulation is determined, as for injected larvae. $LC_{50}$ data (the concentration of virus expressed in polyhedral occlusion bodies/ml of diet required for one half of the larvae to die by 10 days post infection) and $LT_{50}$ data (the time required, at a specific viral concentration, for one half of the larvae to die) are determined.

The effects of recombinant BV are also assessed by feeding polyhedral occlusion bodies to adult insects. Purified polyhedra are applied to insect diet as described above. Dm and Ms adults are allowed to feed on polyhedra-containing food for periods ranging from 2 to 24 hours. Insects are assessed as described above. In addition, after adults are shifted to new containers without polyhedra-containing food, eggs are collected at various intervals. Eggs are allowed to develop, and embryos are assessed for evidence of dsRNA interference effects. In particular, viability of eggs obtained from adults that ingested recombinant BVs designed to inhibit genes whose null phenotype is embryonic lethality is assessed by counting the number of eggs collected at each time point that fail to hatch.

We claim:

1. A pest control agent comprising at least one recombinant baculovirus, wherein the at least one recombinant baculovirus directs transcription of a first ribonucleic acid (RNA) that, when present within an insect cell, hybridizes either with itself or with a second ribonucleic acid whose transcription is directed by the at least one recombinant baculovirus, thereby forming a double-stranded structure that inhibits expression of at least one gene expressed in the insect cell.

2. The pest control agent of claim 1, wherein the first ribonucleic acid hybridizes with itself, thereby forming a double-stranded structure that inhibits expression of at least one gene expressed in the insect cell.

3. The pest control agent of claim 1, wherein the first ribonucleic acid hybridizes with a second ribonucleic acid whose transcription is directed by the at least one recombinant baculovirus, thereby forming a double-stranded structure that inhibits expression of at least one gene expressed in the insect cell.

4. The pest control agent of any of claims 1, 2, or 3, wherein the gene is an endogenous gene.

5. The pest control agent of any of claims 1, 2, or 3, wherein the insect cell is contained in an insect.

6. the pest control agent of any of claims 1, 2, or 3, wherein the insect cell is cultured in vitro.

7. The pest control agent of any of claims 1, 2, and 3, wherein the gene is selected from the group consisting of: genes that are essential in a pest organism, genes involved in neurotransmission in a pest organism, genes involved in development in a pest organism, and genes expressed in the insect alimentary canal or Malpighian tubules.

8. The pest control agent of any of claims 1, 2, and 3, wherein the baculovirus is selected from the group consisting of: the *Autographa californica* multiple polyhedrosis virus, the *Orgyia pseudotsugata* MNPV, the *Lymantria dispar* MNPV, the *Helicoverpa zea* NPV, and the *Bombyx mori* NPV.

9. The pest control agent of claim 5, wherein the insect is a *Lepidopteran*.

10. The pest control agent of claim 9, wherein the insect is selected from the group consisting of: the cotton bollworm (*Helicoverpa zea*), the cabbage looper (*Trichoplusia ni*), the alfalfa looper (*Autographa californica*), the tobacco hornworm (*Manduca sexta*), the tobacco budworm (*Heliothis virescens*), the fall armyworm (*Spodoptera frugiperda*), the European corn borer (*Ostrinia nubilalis*), the eastern spruce budworm (*Choristoneura fumiferana*), the western spruce budworm (*C. occidentalis*), and the gypsy moth (*Lymantria dispar*).

11. The pest control agent of claim 6, wherein the insect cell is a *Lepidopteran* cell.

12. A pest control agent comprising an occlusion body containing a plurality of recombinant baculoviruses, wherein each of the recombinant baculoviruses directs transcription of a first ribonucleic acid (RNA) that, when present within an insect cell, hybridizes either with itself or with a second ribonucleic acid whose transcription is directed by at least one of the recombinant baculoviruses, thereby forming a double-stranded structure that inhibits expression of at least one gene expressed in the insect cell.

13. The pest control agent of claim 12, wherein the first ribonucleic acid hybridizes with itself, thereby forming a double-stranded structure that inhibits expression of at least one gene expressed in the insect cell.

14. The pest control agent of claim 13, wherein the first ribonucleic acid hybridizes with a second ribonucleic acid whose transcription is directed by the at least one recombinant baculovirus, thereby forming a double-stranded structure that inhibits expression of at least one gene expressed in the insect cell.

15. The pest control agent of any of claims 12, 13, or 14, wherein the gene is an endogenous gene.

16. The pest control agent of any of claims 12, 13, or 14, wherein the insect cell is contained in an insect.

17. The pest control agent of any of claims 12, 13, or 14, wherein the insect cell is cultured in vitro.

18. The pest control agent of any of claims 12, 13, and 14, wherein the gene is selected from the group consisting of: genes that are essential in a pest organism, genes involved in neurotransmission in a pest organism, genes involved in development in a pest organism, and genes expressed in the insect alimentary canal or Malpighian tubules.

19. The pest control agent of any of claims 12, 13, and 14, wherein the baculovirus is selected from the group consisting of: the *Autographa californica* multiple polyhedrosis virus, the *Orgyia pseudotsugata* MNPV, the *Lymantria dispar* MNPV, the *Helicoverpa zea* NPV, and the *Bombyx mori* NPV.

20. The pest control agent of claim 16, wherein the insect is a *Lepidopteran*.

21. The pest control agent of claim 20, wherein the insect is selected from the group consisting of: the cotton bollworm (*Helicoverpa zea*), the cabbage looper (*Trichoplusia ni*), the alfalfa looper (*Autographa californica*), the tobacco hornworm (*Manduca sexta*), the tobacco budworm (*Heliothis virescens*), the fall armyworm (*Spodoptera frugiperda*), the European corn borer (*Ostrinia nubilalis*), the eastern spruce budworm (*Choristoneura fumiferana*), the western spruce budworm (*C. occidentalis*), and the gypsy moth (*Lymantria dispar*).

22. The pest control agent of claim 17, wherein the insect cell is a *Lepidopteran* cell.

23. An insecticidal composition comprising the agent of claim 12 and an agriculturally suitable carrier.

24. The composition of claim 23 further comprising at least one agent selected from the group consisting of: conventional pesticides, gustatory stimulants, thickening agents, UV screening agents, optical brighteners, viral synergists, dispersants, flow agents, spreading agents, and sticking agents.

25. A method of continuing insects, the method comprising the step of: contacting a cell in an insect with a first ribonucleic acid (RNA) whose sequence corresponds to at least a portion of at least one gene endogenous to the insect, wherein the first ribonucleic acid hybridizes either with itself or with a second ribonucleic acid with which the cell is also contacted, thereby forming a double-stranded structure within the cell that inhibits expression of at least one gene expressed in the cell, wherein the step of contacting comprises contacting the insect with a baculovirus, and wherein the first RNA is expressed within 6 hours after the insect is contacted with the baculovirus, thereby controlling said insect.

26. A method of controlling insects, the method comprising the step of: contacting a cell in an insect with a first ribonucleic acid (RNA) whose sequence corresponds to at least a portion of at least one gene endogenous to the insect, wherein the first ribonucleic acid hybridizes either with itself or with a second ribonucleic acid with which the cell is also contacted, thereby forming a double-stranded structure within the cell that inhibits expression of at least one gene expressed in the cell, wherein the step of contacting comprises contacting the insect with a baculovirus, and wherein the RNA is expressed substantially in the absence of viral replication, thereby controlling said insect.

27. A method of controlling insects, the method comprising the step of: contacting a cell in an insect with a first ribonucleic acid (RNA) whose sequence corresponds to at least a portion of at least one gene endogenous to the insect, wherein the first ribonucleic acid hybridizes either with itself or with a second ribonucleic acid with which the cell is also contacted, thereby forming a double-stranded structure within the cell that inhibits expression of at least one gene expressed in the cell, wherein the step of contacting comprises contacting the insect with a baculovirus, and wherein the baculovirus does not establish a productive infection, thereby controlling said insect.

28. The method of claim 25, wherein the insect is a *Lepidopteran*.

29. The method of claim 25, wherein the gene is selected from the group consisting of: genes that are essential in a pest organism, genes involved in neurotransmission in a pest organism, genes involved in development in a pest organism, and genes expressed in the insect alimentary canal or Malpighian tubules.

30. The method of claim 25, wherein the baculovirus is selected from the group consisting of: the *Autographa californica* multiple polyhedrosis virus, the *Orgyia pseudotsugata* MNPV, the *Lymantria dispar* MNPV, the *Helicoverpa zea* NPV, and the *Bombyx mori* NPV.

31. The method of claim 25, wherein the step of contacting comprises applying the baculovirus to organisms on which the insect feeds.

32. The method of claim 25, whereby one or more biological or physiological functions of the insect is inhibited.

* * * * *

SEQUENCE LISTING

```
<160> NUMBER OF SEQ ID NOS: 27

<210> SEQ ID NO 1
<211> LENGTH: 230
<212> TYPE: DNA
<213> ORGANISM: Artificial Sequence
<220> FEATURE:
<223> OTHER INFORMATION: Description of Artificial Sequence:SV 40
      Transcriptional Terminator Sequence

<400> SEQUENCE: 1
tgatcataat cagccatacc acatttgtag aggtttact  tgctttaaaa aacctcccac        60
acctccccct gaacctgaaa cataaaatga atgcaattgt tgttgttaac ttgtttattg      120
cagcttataa tggttacaaa taaagcaata gcatcacaaa tttcacaaat aaagcatttt      180
tttcactgca ttctagttgt ggtttgtcca aactcatcaa tgtatcttaa                 230

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:Primer used
      in Construction of Modified Baculovirus Transfer Vectors

<400> SEQUENCE: 2
aaaatctaga tcataatcag ccatacc                                           27

<210> SEQ ID NO 3
<211> LENGTH: 29
```

```
<212> TYPE: DNA
<213> ORGANISM: Artificial Sequence
<220> FEATURE:
<223> OTHER INFORMATION: Description of Artificial Sequence:Primers
      used in Construction of Modified Baculovirus Transfer Vectors

<400> SEQUENCE: 3
ccgcggttaa gatacattga tgagtttgg                                    29

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:Primers used
      in Construction of Modified Baculovirus Transfer Vectors

<400> SEQUENCE: 4
aaaaggatcc attgatgagt ttggacaaac c                                 31

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:Primers
      used in Construction of Modified Baculovirus Transfer Vectors

<400> SEQUENCE: 5
actagttatc tccatgatgg gcgcg                                        25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:Primers
      used in Construction of Modified Baculovirus Transfer Vectors

<400> SEQUENCE: 6
agatctatat agttgctgat gggcgcg                                      27

<210> SEQ ID NO 7
<211> LENGTH: 55
<212> TYPE: DNA
<213> ORGANISM: Artificial Sequence
<220> FEATURE:
<223> OTHER INFORMATION: Description of Artificial Sequence:Portion of
      Multiple Cloning Site from Plasmid PCR2.1
      Incorporated into Modified Baculovirus Transfer
      Plasmids

<400> SEQUENCE: 7
agccgaattc tgcagatatc catcacactg gcggccgctc gagcatgcat ctaga       55

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Drosphila
      Melanogaster

<400> SEQUENCE: 8
tgaggaagaa cgcagtttgt tcc                                          23

<210> SEQ ID NO 9
```

```
<211> LENGTH: 21
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Drosphila
      Melanogaster

<400> SEQUENCE: 9
cgggcataaa atgaaacctc g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Drosophila
      Melanogaster

<400> SEQUENCE: 10
cgctgtgaca catactttct g                                              21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Drosophila
      Melanogaster

<400> SEQUENCE: 11
gtcttagagc cagatatgcg                                                20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Drosophila
      Melanogaster

<400> SEQUENCE: 12
tctccacctc ctgcaatatc cg                                             22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Primers
      used to Amplify Portions of Target Genes from Drosophila
      Melanogaster

<400> SEQUENCE: 13
cccattcact cttgtgacca gag                                            23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Drosophila
      Melanogaster

<400> SEQUENCE: 14
```
accagaaaga gaaccagcat caac                                                    24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Drosophila
      Melanogaster

<400> SEQUENCE: 15
acctgccagc ggtctgtaaa ag                                                      22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 16
tgcatggaat tggcttgact tc                                                      22

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 17
agcaccagtt gatagagatt ctccc                                                   25

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 18
ctcgttctta ttccctccta ac                                                      22

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 19
atgaacgggt cgttgtacc                                                          19

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 20

-continued tactgcacca gaaatggaag agc                     23

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 21
acgggttggt tgttcatagc c                       21

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 22
cgtgcaacgt gctcgttttt ac                      22

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 23
ttaggagttg taggaggcat cgg                     23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 24
gatctggttt cgattgtttc cg                      22

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manuca Sexta

<400> SEQUENCE: 25
cgaggaccaa ctcaatttgg aatg                    24

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 26

```
ggtgacccac attcactcgt tatac                                        25

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:Primers
      used to Amplify Portions of Target Genes from Manduca Sexta

<400> SEQUENCE: 27
aacctacaga cctcaatgcc tcc                                          23
```